(12) United States Patent
Henry et al.

(10) Patent No.: US 10,004,867 B2
(45) Date of Patent: Jun. 26, 2018

(54) RESPIRATORY APPARATUS

(71) Applicant: ResMed Limited, Bella Vista (AU)

(72) Inventors: Robert Edward Henry, Baulkham Hills (AU); Rupert Christian Scheiner, Davidson (AU); Lance Ian Swift, Coogee (AU); Matthew Robin Wells, Manly (AU)

(73) Assignee: ResMed Limited (AU)

( * ) Notice: Subject to any disclaimer, the term of this patent is extended or adjusted under 35 U.S.C. 154(b) by 600 days.

(21) Appl. No.: 14/172,437

(22) Filed: Feb. 4, 2014

(65) Prior Publication Data

US 2014/0224253 A1 Aug. 14, 2014

(30) Foreign Application Priority Data

Feb. 4, 2013 (AU) ............................... 2013900348

(51) Int. Cl.
*A61M 16/06* (2006.01)
*A61M 16/08* (2006.01)
(Continued)

(52) U.S. Cl.
CPC ...... *A61M 16/0633* (2014.02); *A61M 16/024* (2017.08); *A61M 16/0616* (2014.02);
(Continued)

(58) Field of Classification Search
CPC ..................... A61M 16/0616; A61M 16/0683
(Continued)

(56) References Cited

U.S. PATENT DOCUMENTS 4,323,063 A 4/1982 Fisichella
4,782,832 A 11/1988 Trimble et al.
(Continued)

FOREIGN PATENT DOCUMENTS

EP 0288937 A2 11/1988
EP 0288938 A2 11/1988
(Continued)

OTHER PUBLICATIONS

International Search Report & Written Opinion for Application No. PCT/AU2014/000077 dated Apr. 23, 2014.
(Continued)

*Primary Examiner* — Peter S Vasat
*Assistant Examiner* — Margaret Luarca
(74) *Attorney, Agent, or Firm* — Botos Churchill IP Law LLP

(57) ABSTRACT

A mask apparatus for a respiratory treatment can permit delivery of breathable gas to a user. In one example, the mask may employ a frame and cushion to form a seal for both mouth and nose. The frame may be adapted for coupling with a respiratory treatment apparatus so as to permit communication of a pressurized gas from the respiratory treatment apparatus. The cushion, which may be foam, may have a substantially under the nose configuration. The mask may have a common plenum chamber for both nose and mouth. The cushion may further define a centrally open lip superior region. The cushion may be adapted to couple with the frame directly or to the frame in conjunction with a cushion support clip. Various features of the cushion may further promote sealing and comfort for the under the nose design.

30 Claims, 36 Drawing Sheets

(51) Int. Cl.
*A61M 16/00* (2006.01)
*A61M 16/10* (2006.01)

(52) U.S. Cl.
CPC ..... *A61M 16/0683* (2013.01); *A61M 16/0069* (2014.02); *A61M 16/0816* (2013.01); *A61M 16/107* (2014.02); *A61M 2016/0027* (2013.01); *A61M 2016/0039* (2013.01)

(58) Field of Classification Search
USPC .................................................. 128/205.25
See application file for complete search history.

(56) References Cited

U.S. PATENT DOCUMENTS

| | | | |
|---|---|---|---|
| 4,803,981 A | 2/1989 | Vickery | |
| 4,944,310 A | 7/1990 | Sullivan | |
| 4,945,907 A | 8/1990 | Tayebi | |
| 5,429,683 A | 7/1995 | Le Mitouard | |
| 6,196,223 B1 | 3/2001 | Belfer et al. | |
| 6,532,959 B1 | 3/2003 | Berthon-Jones | |
| 6,581,594 B1 | 6/2003 | Drew et al. | |
| 7,152,602 B2 | 12/2006 | Bateman et al. | |
| 7,448,386 B2 | 11/2008 | Ho et al. | |
| D582,546 S | 12/2008 | Fujiura et al. | |
| 7,472,703 B2 | 1/2009 | Hernandez et al. | |
| 7,546,837 B2 | 6/2009 | Busch | |
| 7,575,006 B2 | 8/2009 | Schegerin | |
| 7,708,017 B2 | 5/2010 | Davidson et al. | |
| 8,028,699 B2 | 10/2011 | Ho et al. | |
| 8,220,459 B2 | 7/2012 | Davidson et al. | |
| 8,347,886 B2 | 1/2013 | Ho et al. | |
| D693,460 S | 11/2013 | Rothermel et al. | |
| D693,462 S | 11/2013 | Rothermel et al. | |
| 8,701,667 B1 | 4/2014 | Ho et al. | |
| 8,869,797 B2 | 10/2014 | Davidson et al. | |
| D751,188 S | 3/2016 | Skipper et al. | |
| D769,440 S | 10/2016 | Amarasinghe et al. | |
| 2002/0029780 A1 | 3/2002 | Frater et al. | |
| 2003/0168063 A1 | 9/2003 | Gambone et al. | |
| 2005/0199242 A1 | 9/2005 | Matula et al. | |
| 2005/0257792 A1 | 11/2005 | Wixey et al. | |
| 2006/0118117 A1* | 6/2006 | Berthon-Jones ...... | A61M 16/06 128/206.21 |
| 2007/0006879 A1 | 1/2007 | Thornton | |
| 2007/0125385 A1* | 6/2007 | Ho ........................ | A61M 16/06 128/206.26 |
| 2007/0125386 A1 | 6/2007 | Quinn | |
| 2007/0145534 A1 | 6/2007 | Murakami | |
| 2007/0215161 A1 | 9/2007 | Frater et al. | |
| 2008/0257354 A1 | 10/2008 | Davidson et al. | |
| 2009/0014007 A1 | 1/2009 | Brambilla et al. | |
| 2009/0044808 A1 | 2/2009 | Guney et al. | |
| 2009/0050156 A1 | 2/2009 | Ng et al. | |
| 2009/0139525 A1 | 6/2009 | Schirm | |
| 2009/0255542 A1 | 10/2009 | Ugai et al. | |
| 2010/0000534 A1 | 1/2010 | Kooij et al. | |
| 2010/0028425 A1 | 2/2010 | Mehta et al. | |
| 2010/0108072 A1* | 5/2010 | D'Souza ............... | A61M 16/06 128/206.24 |
| 2010/0319700 A1* | 12/2010 | Ng ........................ | A61M 16/06 128/206.28 |
| 2011/0005524 A1 | 1/2011 | Veliss et al. | |
| 2011/0088698 A1 | 4/2011 | Barnett et al. | |
| 2011/0146684 A1 | 6/2011 | Wells et al. | |
| 2011/0209701 A1 | 9/2011 | Derringer et al. | |
| 2012/0080035 A1 | 4/2012 | Guney et al. | |
| 2012/0204879 A1 | 8/2012 | Cariola et al. | |
| 2012/0204881 A1 | 8/2012 | Davidson et al. | |
| 2012/0222680 A1 | 9/2012 | Eves et al. | |
| 2013/0104902 A1 | 5/2013 | Ho et al. | |
| 2013/0199537 A1* | 8/2013 | Formica ............... | A61M 16/06 128/205.25 |
| 2014/0216462 A1 | 8/2014 | Law et al. | |
| 2014/0261435 A1 | 9/2014 | Rothermel | |
| 2014/0290663 A1 | 10/2014 | Rothermel | |
| 2014/0311496 A1 | 10/2014 | Rothermel | |
| 2015/0000671 A1 | 1/2015 | Frerichs et al. | |
| 2015/0328423 A1* | 11/2015 | Siew .................... | A61M 16/06 128/205.25 |
| 2016/0325067 A1 | 11/2016 | Harwood et al. | |

FOREIGN PATENT DOCUMENTS

| | | |
|---|---|---|
| EP | 0427474 A2 | 5/1991 |
| EP | 2213324 A1 | 8/2010 |
| EP | 2428241 A1 | 3/2012 |
| GB | 2385533 A | 8/2003 |
| JP | 2012501763 A | 1/2012 |
| TW | M253360 U | 12/2004 |
| TW | I357340 B | 2/2012 |
| WO | 97/09090 A1 | 3/1997 |
| WO | 1998004310 A1 | 2/1998 |
| WO | 19980034665 A1 | 8/1998 |
| WO | 9925410 A1 | 5/1999 |
| WO | 200000078381 A1 | 12/2000 |
| WO | 0195965 A1 | 12/2001 |
| WO | 2004007010 A1 | 1/2004 |
| WO | 2004041342 A1 | 5/2004 |
| WO | 2004073778 A1 | 9/2004 |
| WO | 2005063328 A1 | 7/2005 |
| WO | 20060074513 A1 | 7/2006 |
| WO | 2006130903 A1 | 12/2006 |
| WO | 2007009182 A1 | 1/2007 |
| WO | 2007133332 A2 | 11/2007 |
| WO | 2008011682 A1 | 1/2008 |
| WO | 2008011683 A1 | 1/2008 |
| WO | 2008070929 A1 | 6/2008 |
| WO | 2009052560 A1 | 4/2009 |
| WO | 2009108994 A1 | 9/2009 |
| WO | 2009109004 A1 | 9/2009 |
| WO | 2010028425 A1 | 3/2010 |
| WO | 2010148453 A1 | 12/2010 |
| WO | 201000135785 A1 | 12/2010 |
| WO | 2011060479 A1 | 5/2011 |
| WO | 2012177152 A1 | 12/2012 |
| WO | 2016054692 A2 | 4/2016 |

OTHER PUBLICATIONS

Supplementary European Search Report for Application No. EP14746612 dated Sep. 26, 2016.

Japanese Patent Application No. 2015-555500 Office Action dated Dec. 8, 2017.

* cited by examiner

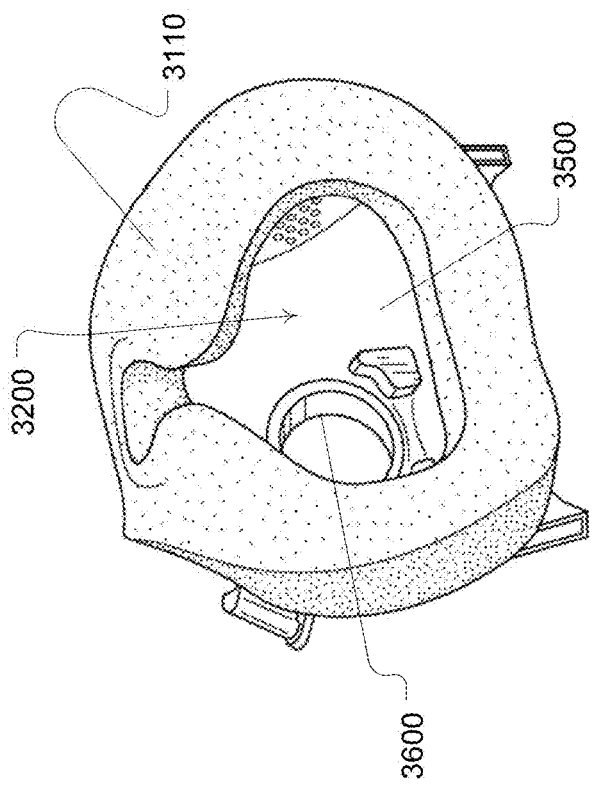
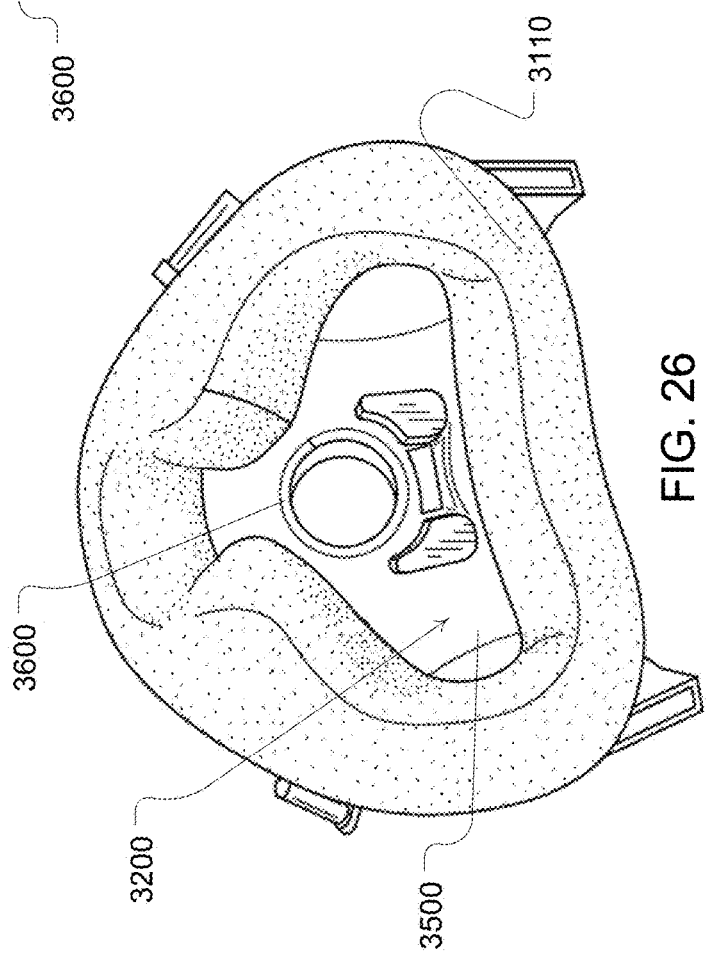
FIG. 26
FIG. 27

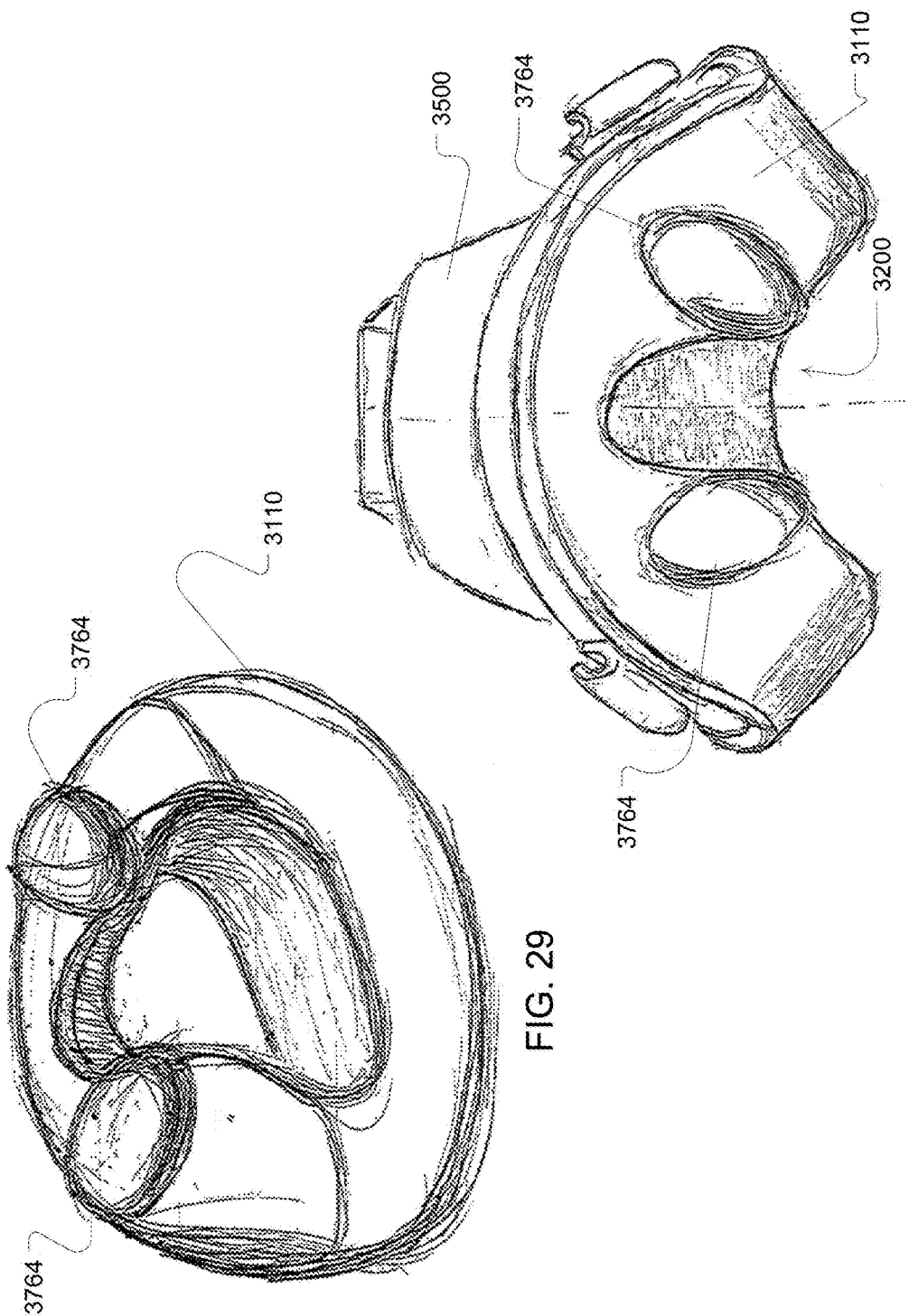

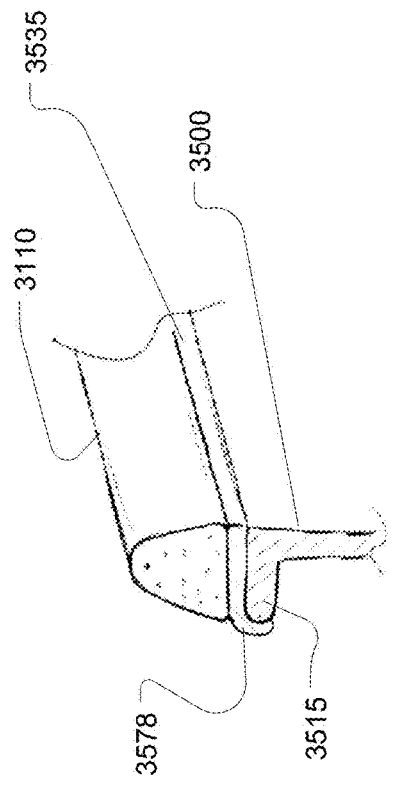
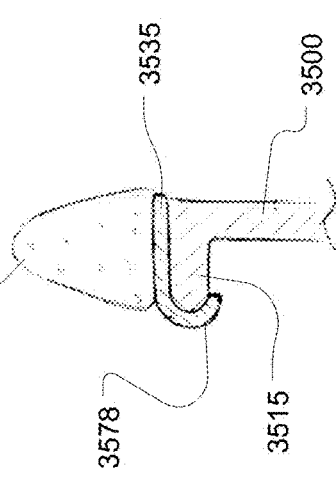
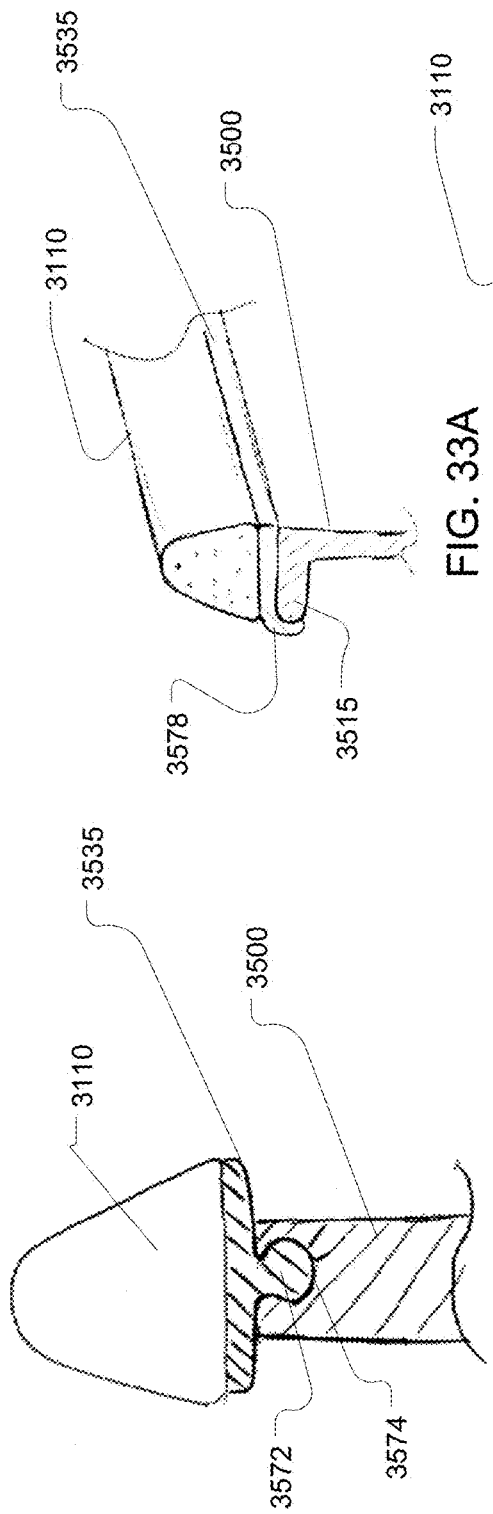
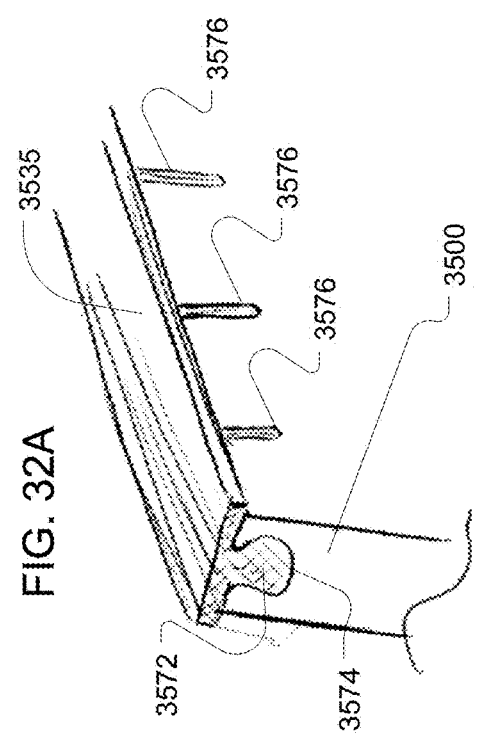

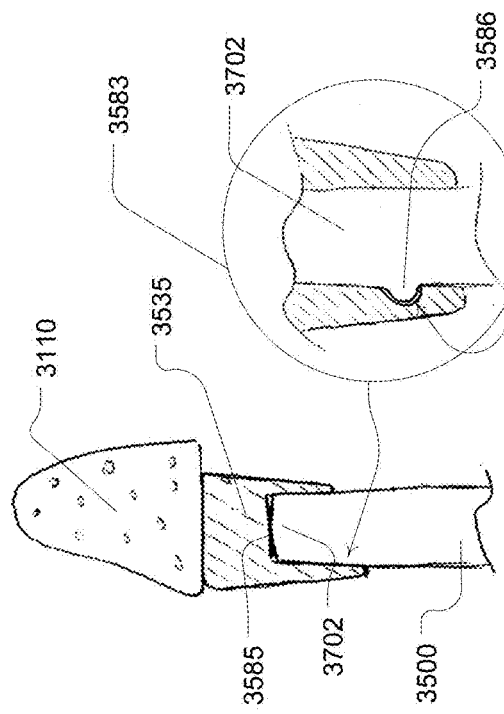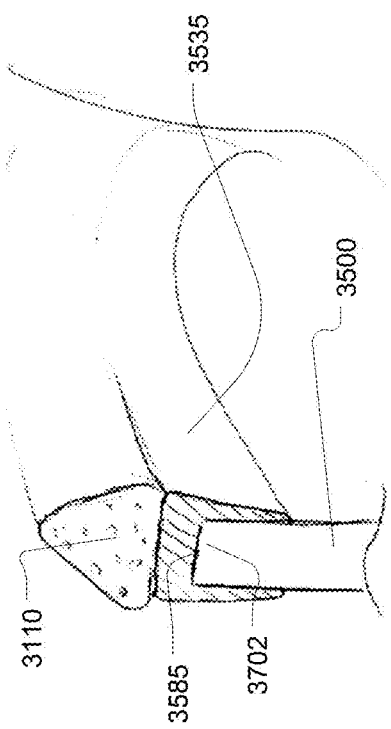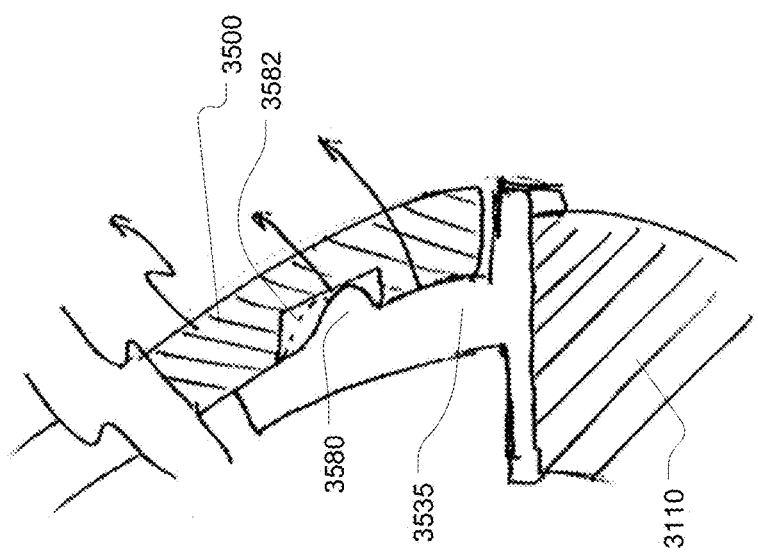

RESPIRATORY APPARATUS

CROSS-REFERENCE TO RELATED APPLICATIONS

The present application claims priority from Australian Provisional Patent Application No. 2013900348 filed Feb. 4, 2013, the disclosure of which is hereby incorporated herein by reference.

BACKGROUND OF THE TECHNOLOGY

Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders. Such devices may include an interface for directing a treatment to a patient respiratory system.

Description of the Related Art

The respiratory system of the body facilitates gas exchange. The nose and mouth form the entrance to the airways of a patient.

The airways consist of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnoea on exertion, chronic cough and sputum production.

Neuromuscular Disease (NMD) may encompass many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnoea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnoea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

Patient Interface

The application of a supply of air at positive pressure to an entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may consist of an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2:2007, 10 cmH$_2$O pressure at 1 m).

| Mask name | Mask type | A-weighted sound power level dbA (uncertainty) | A-weighted sound pressure dbA (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |
| ResMed Mirage series I, II (*) | full face | 31.7 | 23.7 | 2000 |
| ResMed UltraMirage | full face | 35 (3) | 27 (3) | 2004 |
| ResMed Mirage Quattro | full face | 26 (3) | 18 (3) | 2006 |
| ResMed Mirage Quattro FX | full face | 27 (3) | 19 (3) | 2008 |

((*) one specimen only, measured using test method specified in ISO3744 in CPAP mode at 10 cmH$_2$O)

Sound pressure values of a variety of objects are listed below

| Object | A-weighted sound pressure dbA (uncertainty) | Notes |
| --- | --- | --- |
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), U.S. Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, treatment or prevention of a respiratory disorder.

Another aspect of the present technology relates to methods used in the diagnosis, treatment or prevention of a respiratory disorder.

One form of the present technology involves an interface that directs a treatment, such as a positive pressure breathable gas, to a patient respiratory system.

Another aspect of one form of the present technology involves such an interface that directs a treatment to the nares of the patient respiratory system.

Another aspect of one form of the present technology is such an interface that directs a treatment to the nares and mouth of the patient respiratory system but maintaining a minimal facial contact profile so as to avoid contact or coverage of a majority of a nose of patient.

Another aspect of one form of the present technology is a patient interface that is moulded or otherwise constructed with a clearly defined perimeter shape which is intended to match that of an intended wearer.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

Treatment Systems

Therapy

Respiratory System

Figure 1A:
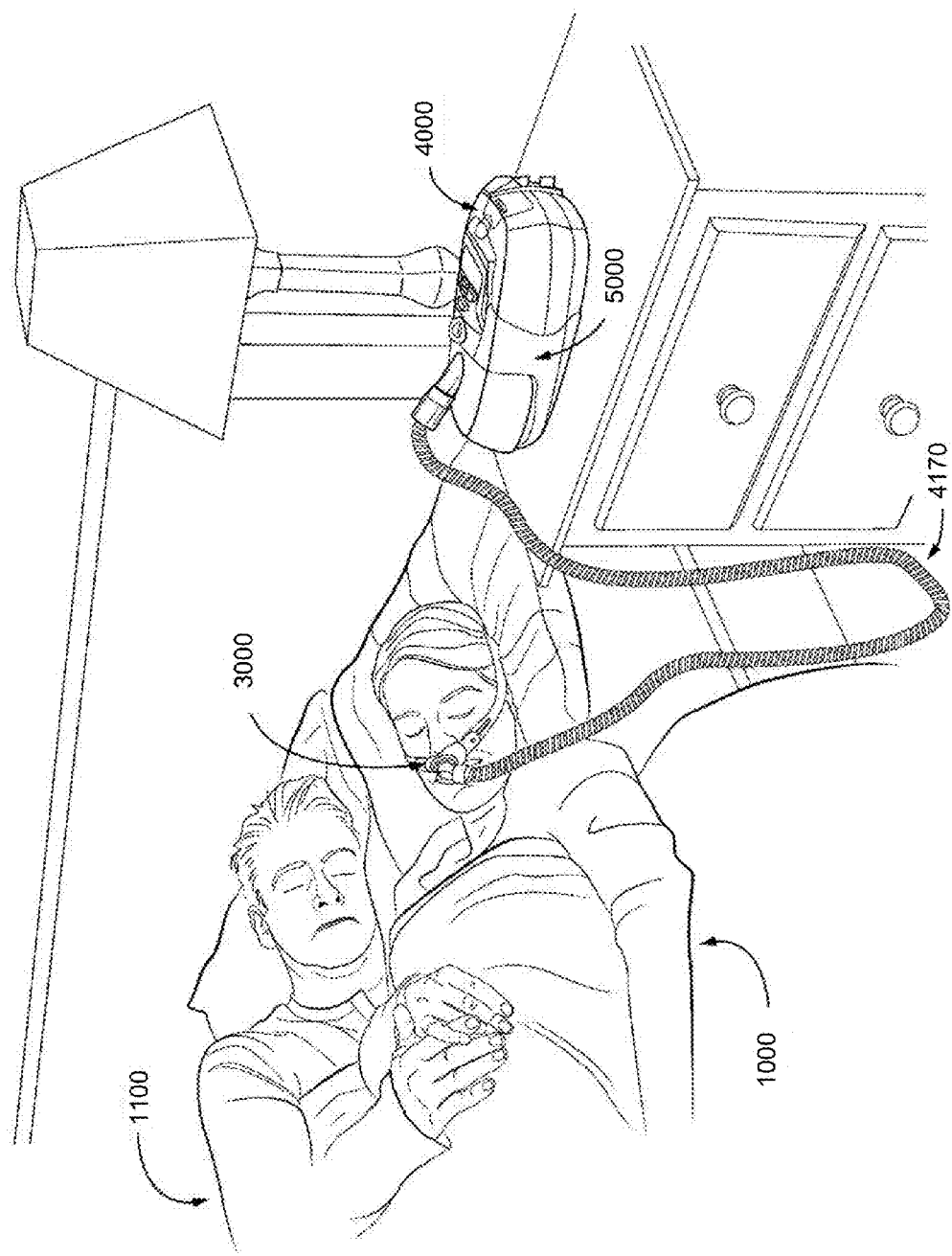
FIG. 1a shows components of a system suitable for use with examples of the present technology. A patient 1000 wearing a patient interface 3000, such as nasal prongs only covering the patient's nose, receives a supply of air at positive pressure from a PAP device 4000. Air from the PAP device is humidified in a humidifier 5000, and passes along an air circuit 4170 to the patient 1000.
Figure 1B:
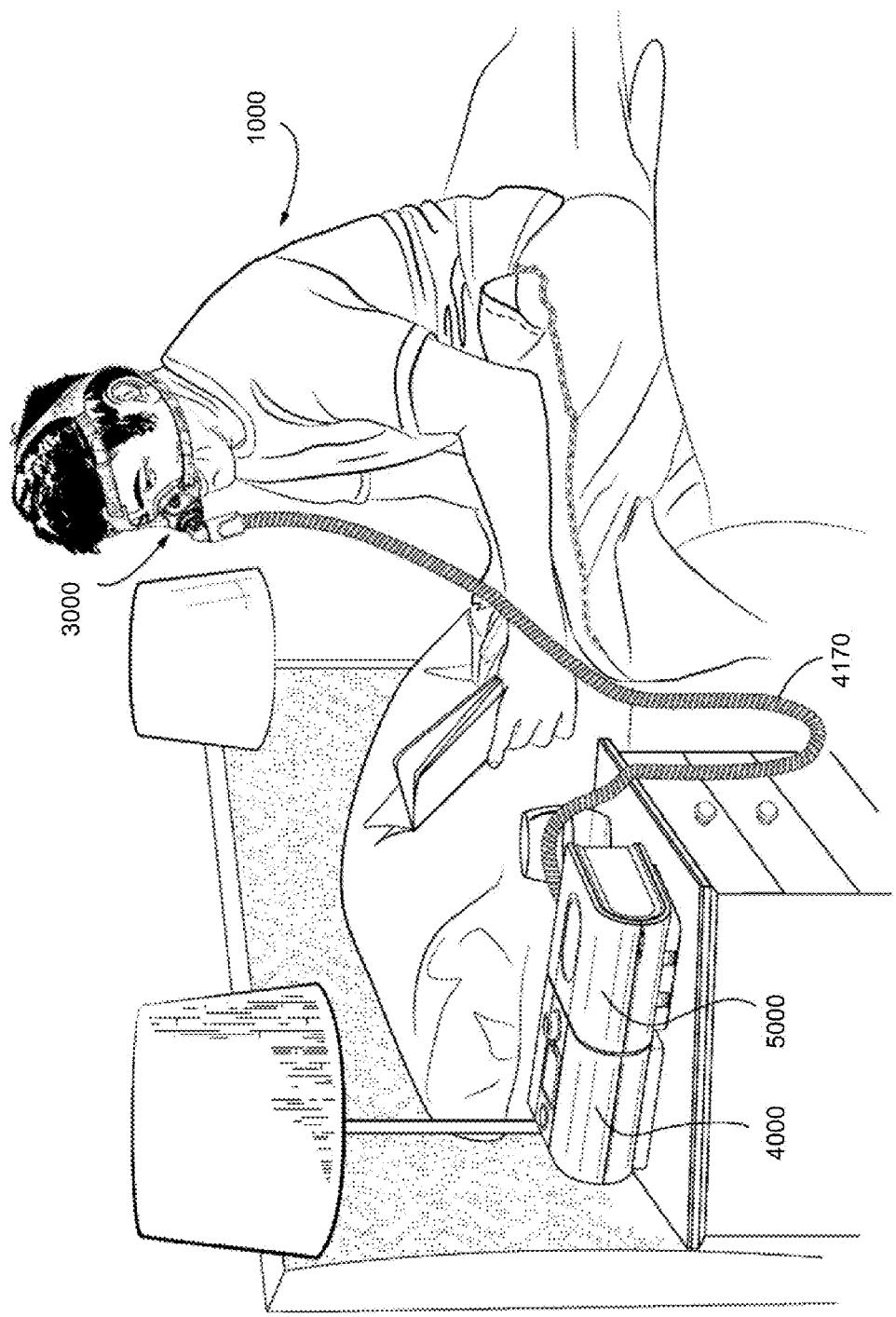
FIG. 1b shows a PAP device 400 in use on a patient with a nasal mask type of patient interface.
Figure 1C:
FIG. 1c shows a PAP device in use on a patient with a full-face mask type of patient interface.
Figure 2A:
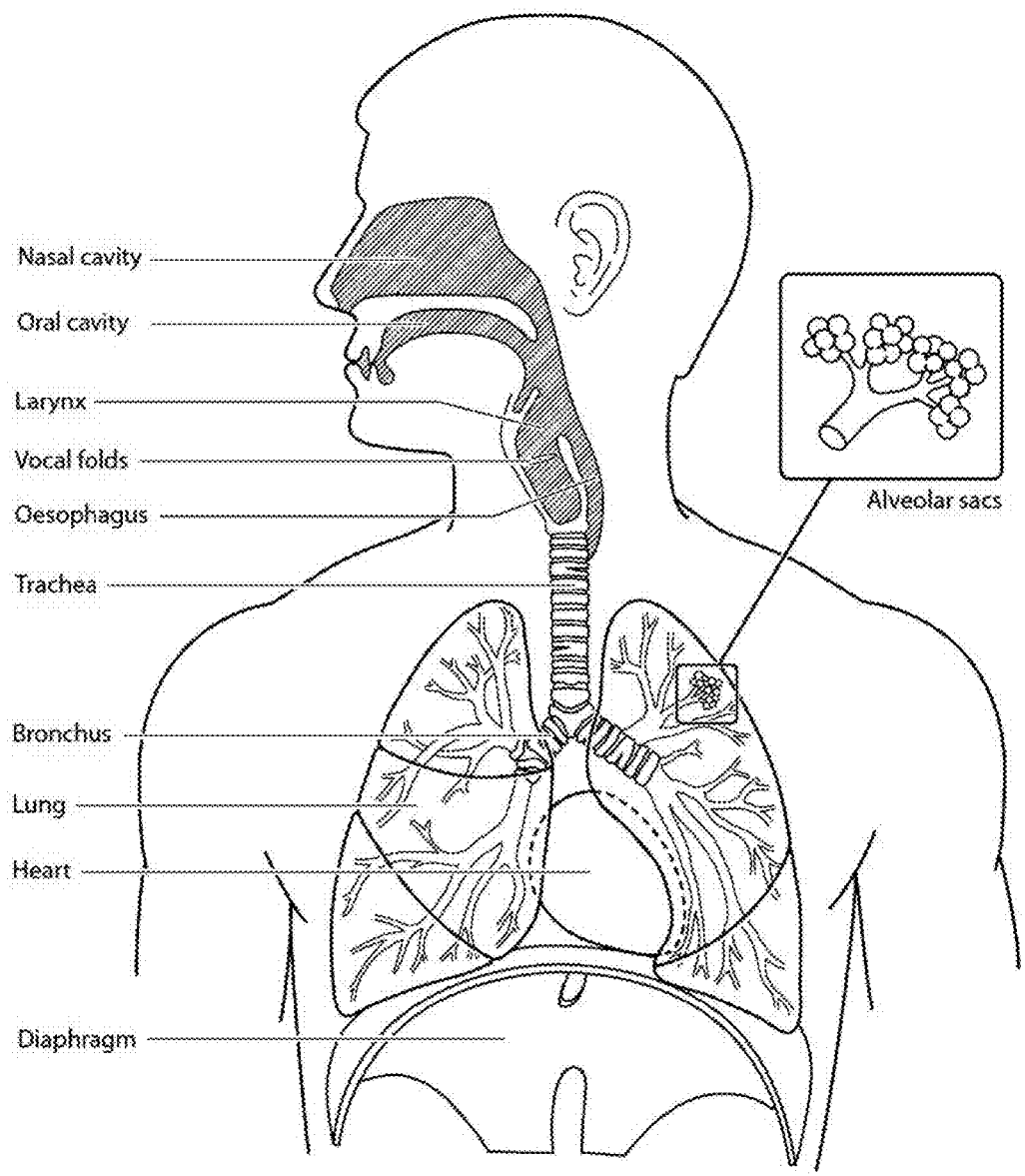
Figure 2B:
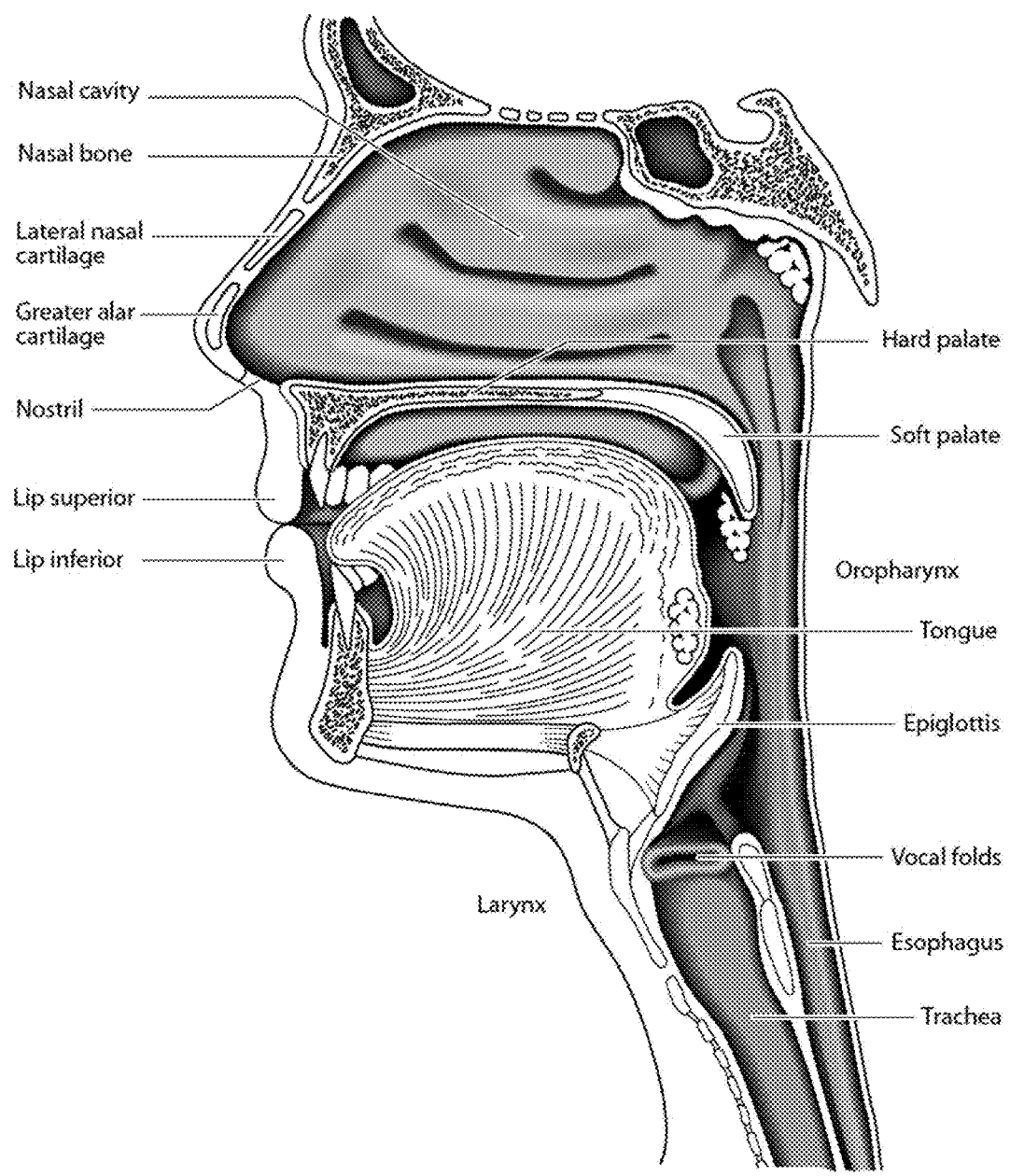

FIG. 2a shows an overview of a human respiratory system including the nasal and oral cavities, the larynx, vocal folds, oesophagus, trachea, bronchus, lung, alveolar sacs, heart and diaphragm;

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea;

Facial Anatomy

Figure 2C:
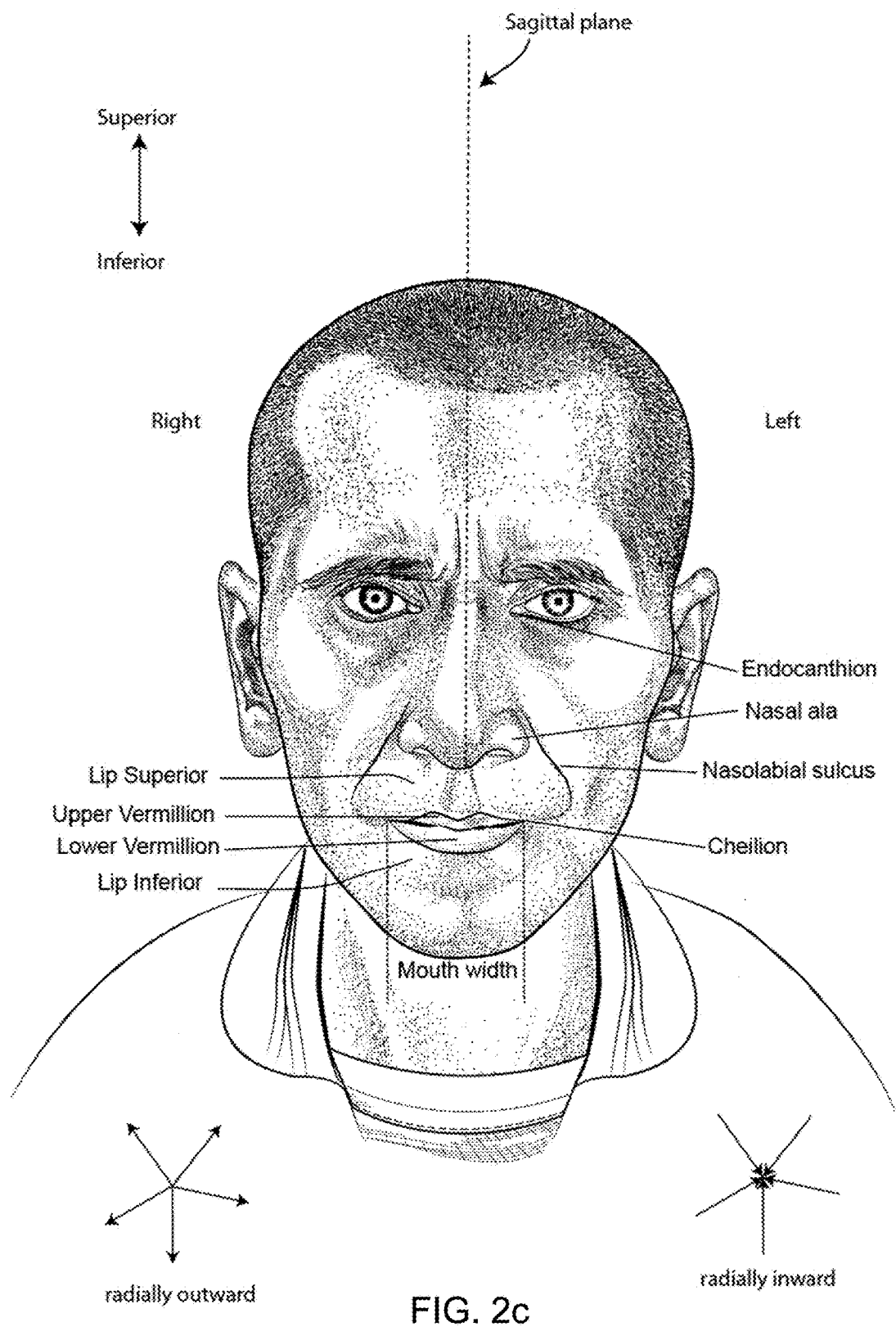
Figure 2D:
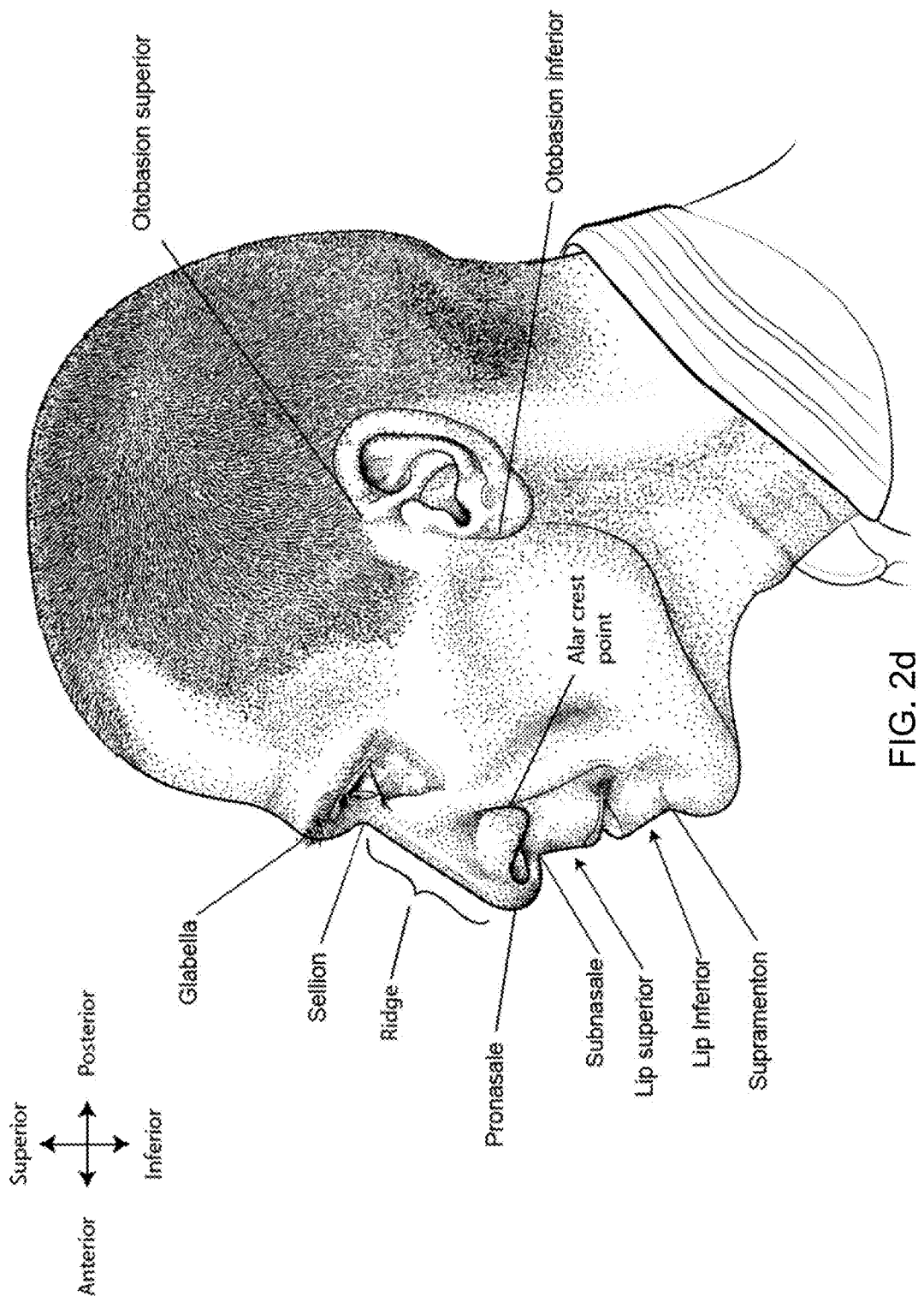
Figure 2E:
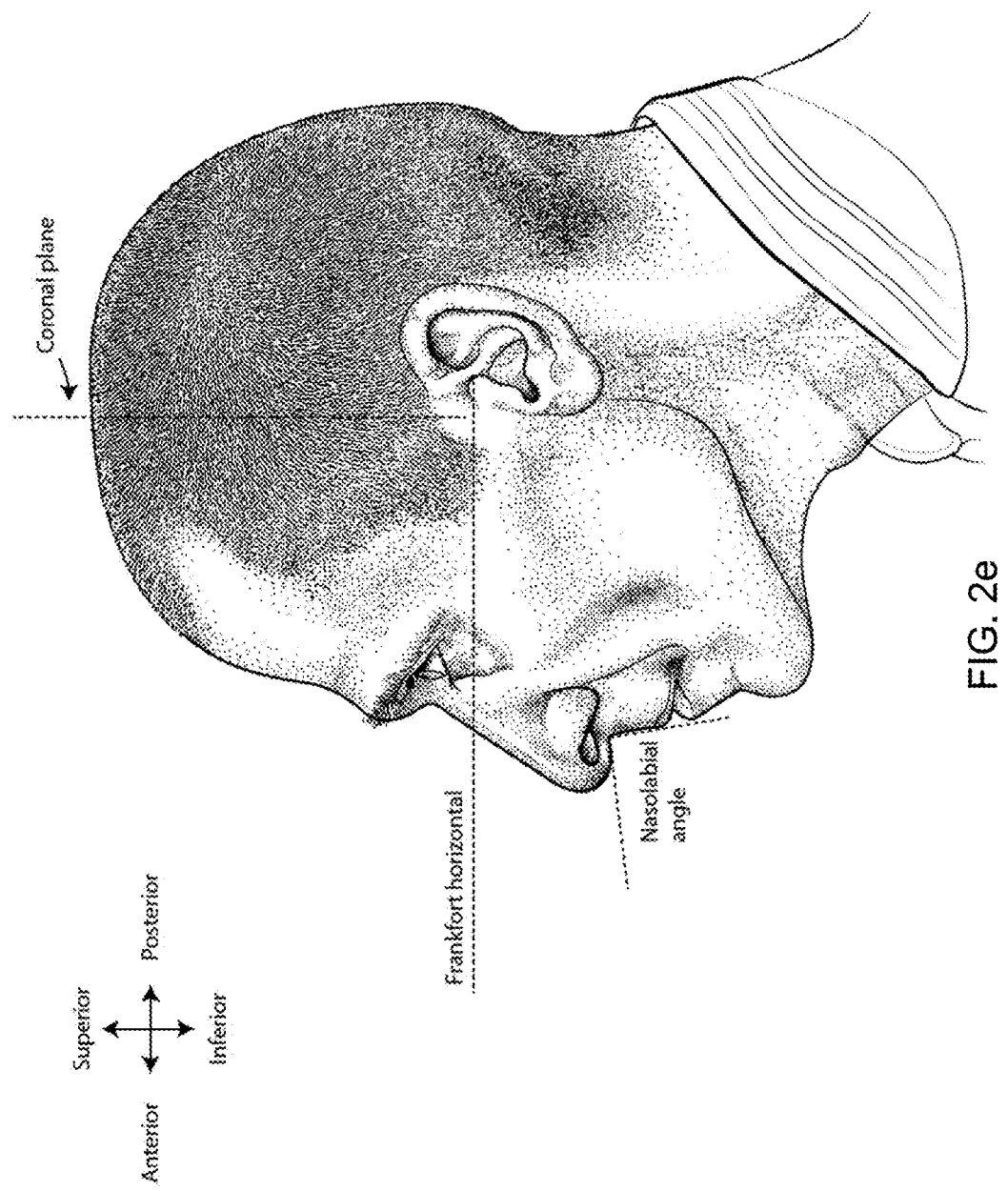
Figure 2F:
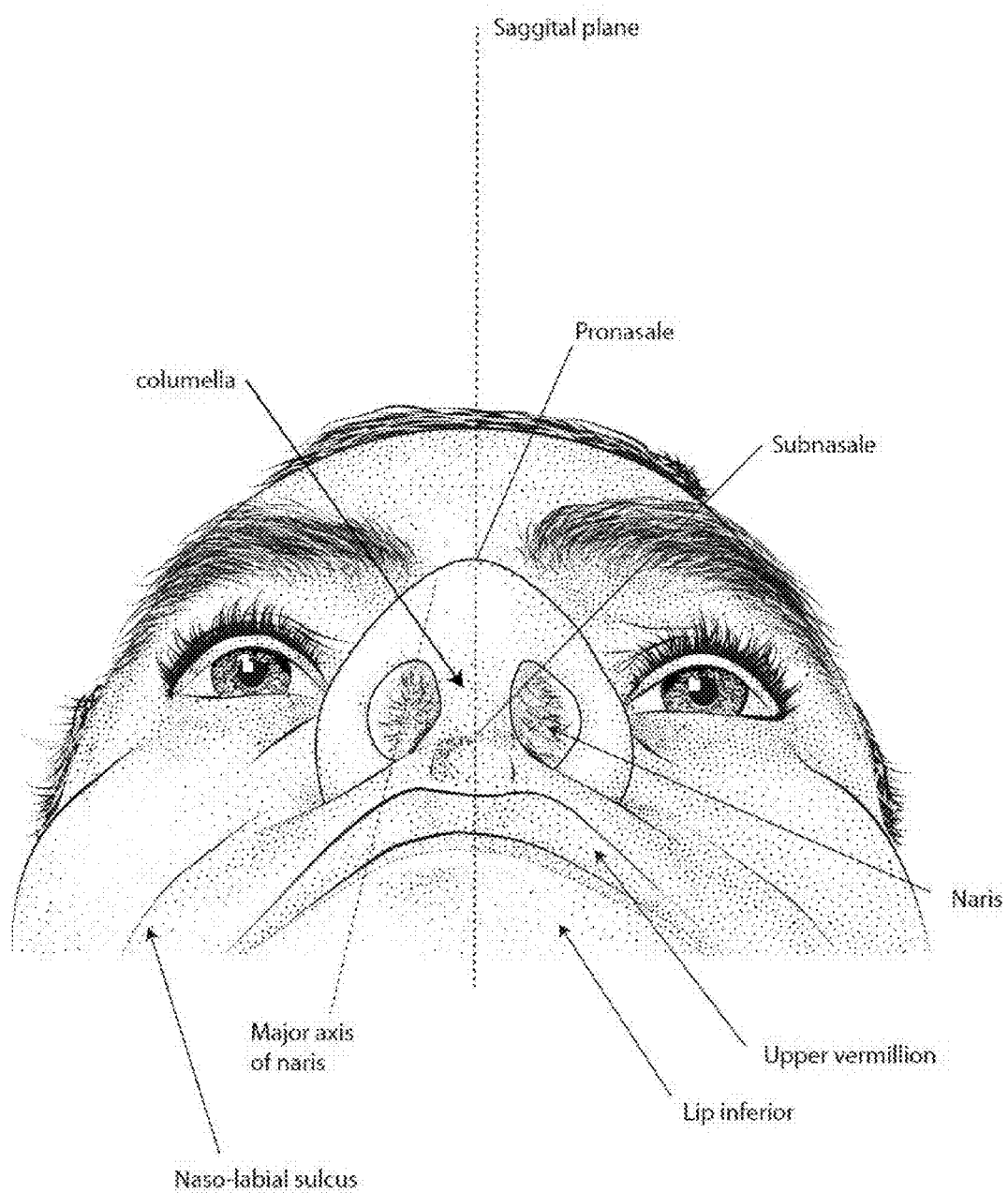
Figure 2I:
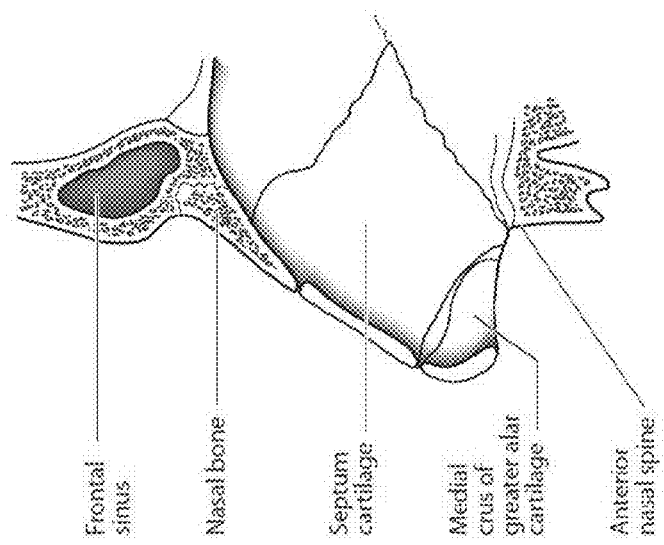
Figure 2H:
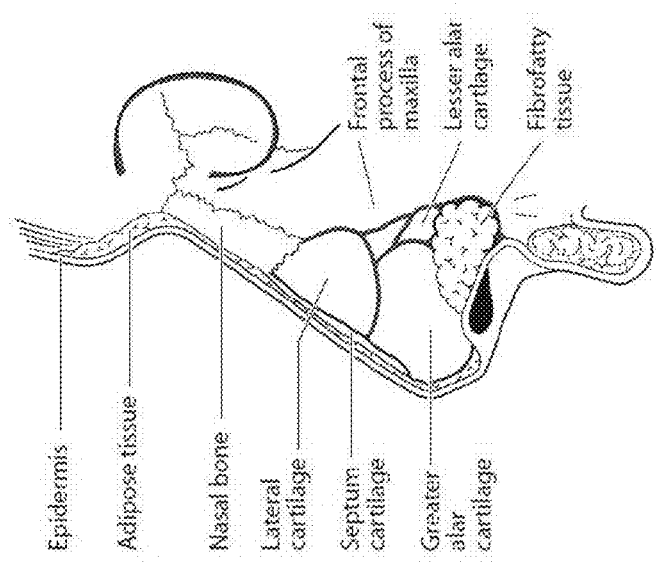
Figure 2G:
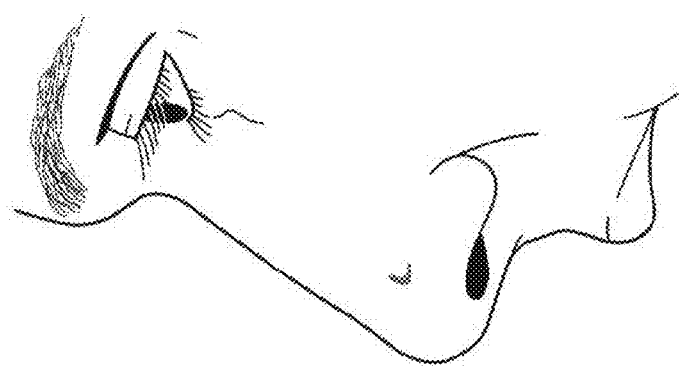
Figures 2J, 2K:
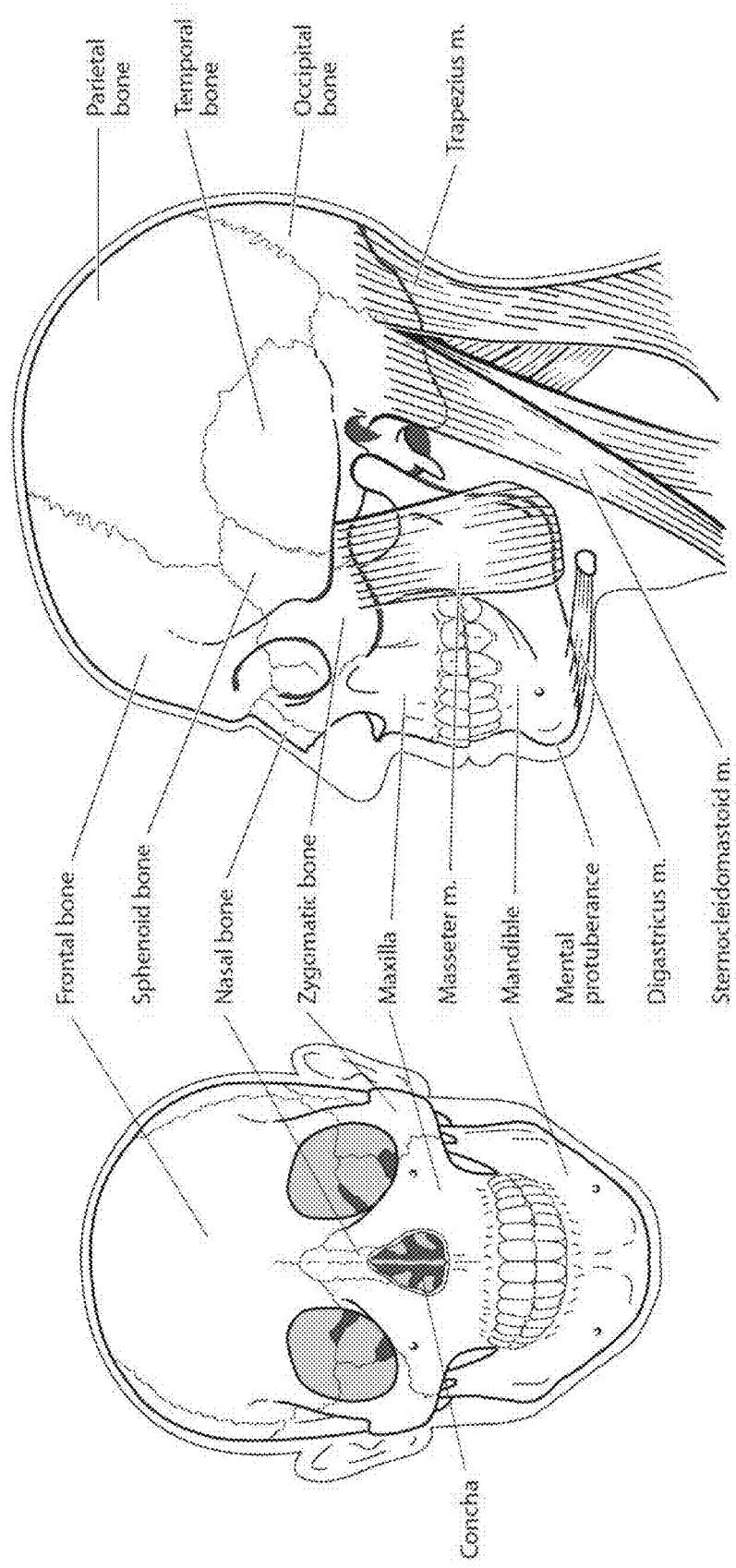

FIG. 2c is a front view of a face with several features of surface anatomy identified including the lip superior, upper vermillion, lower vermillion, lip inferior, mouth width, endocanthion, a nasal ala, nasolabial sulcus and cheilion;

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior;

FIG. 2e is a further side view of a head. The approximate locations of the Frankfort horizontal and nasolabial angle are indicated;

FIG. 2f shows a base view of a nose;

FIG. 2g shows a side view of the superficial features of a nose;

FIG. 2h shows subcutaneal structures of the nose, including lateral cartilage, septum cartilage, greater alar cartilage, lesser alar cartilage and fibrofatty tissue;

FIG. 2i shows a medial dissection of a nose, approximately several millimeters from a sagittal plane, amongst other things showing the septum cartilage and medial crus of greater alar cartilage;

FIG. 2j shows a front view of the bones of a skull including the frontal, temporal, nasal and zygomatic bones. Nasal concha are indicated, as are the maxilla, mandible and mental protuberance;

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius;

PAP Device

Figure 3:
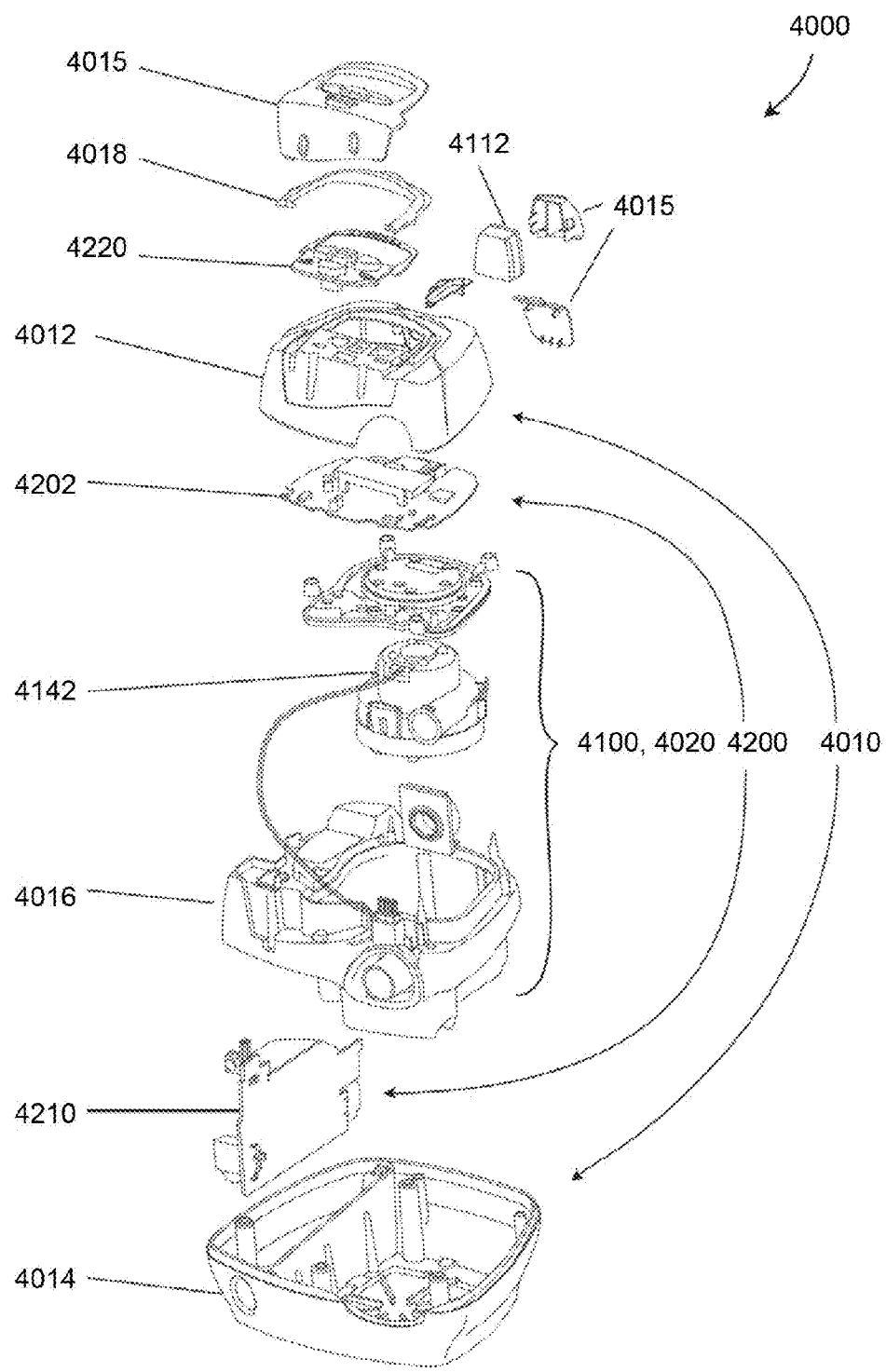

FIG. 3 shows an example PAP device suitable for implementation with examples of the present technology;

Patient Interface

Figure 4:
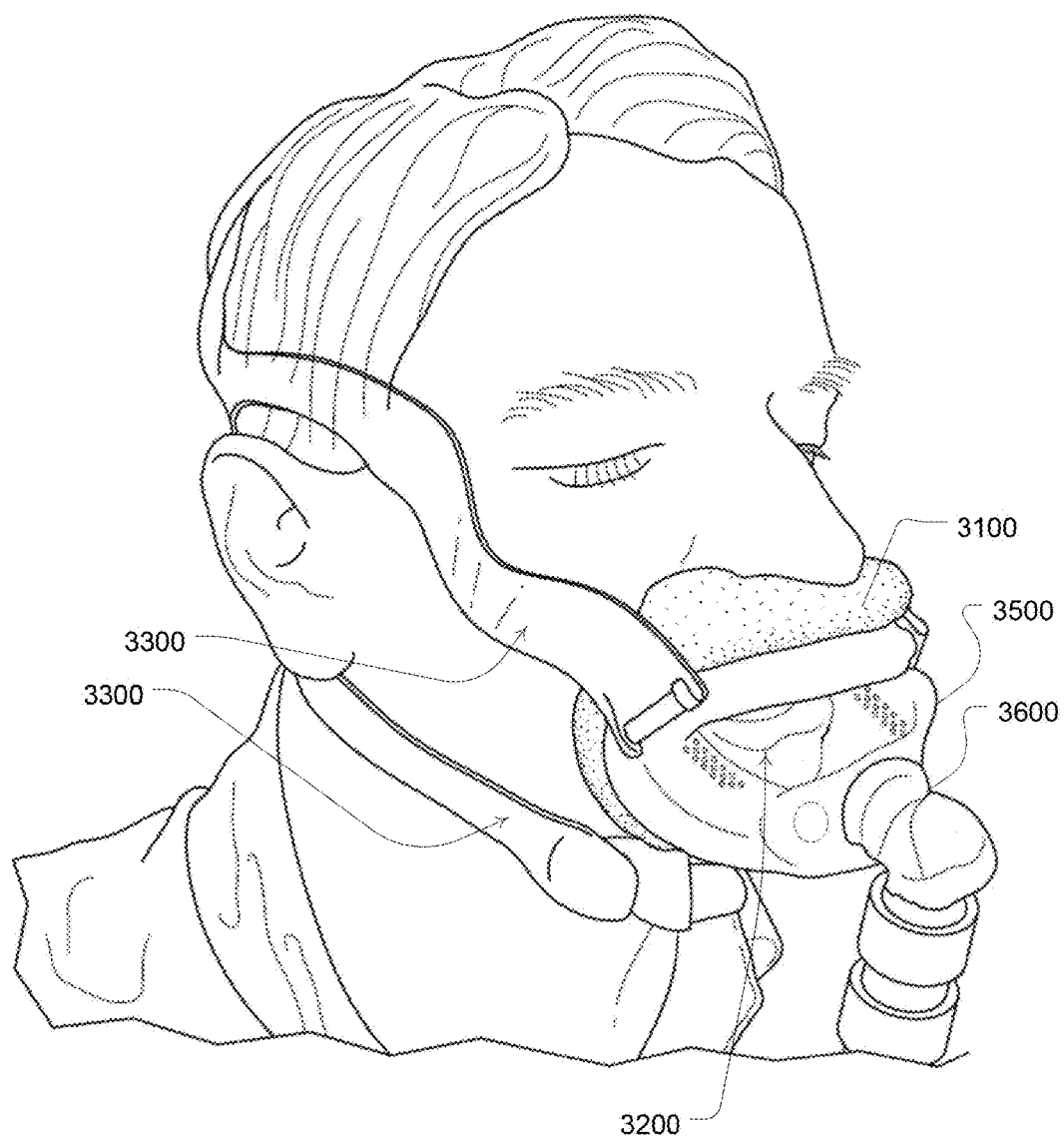
Figure 5:
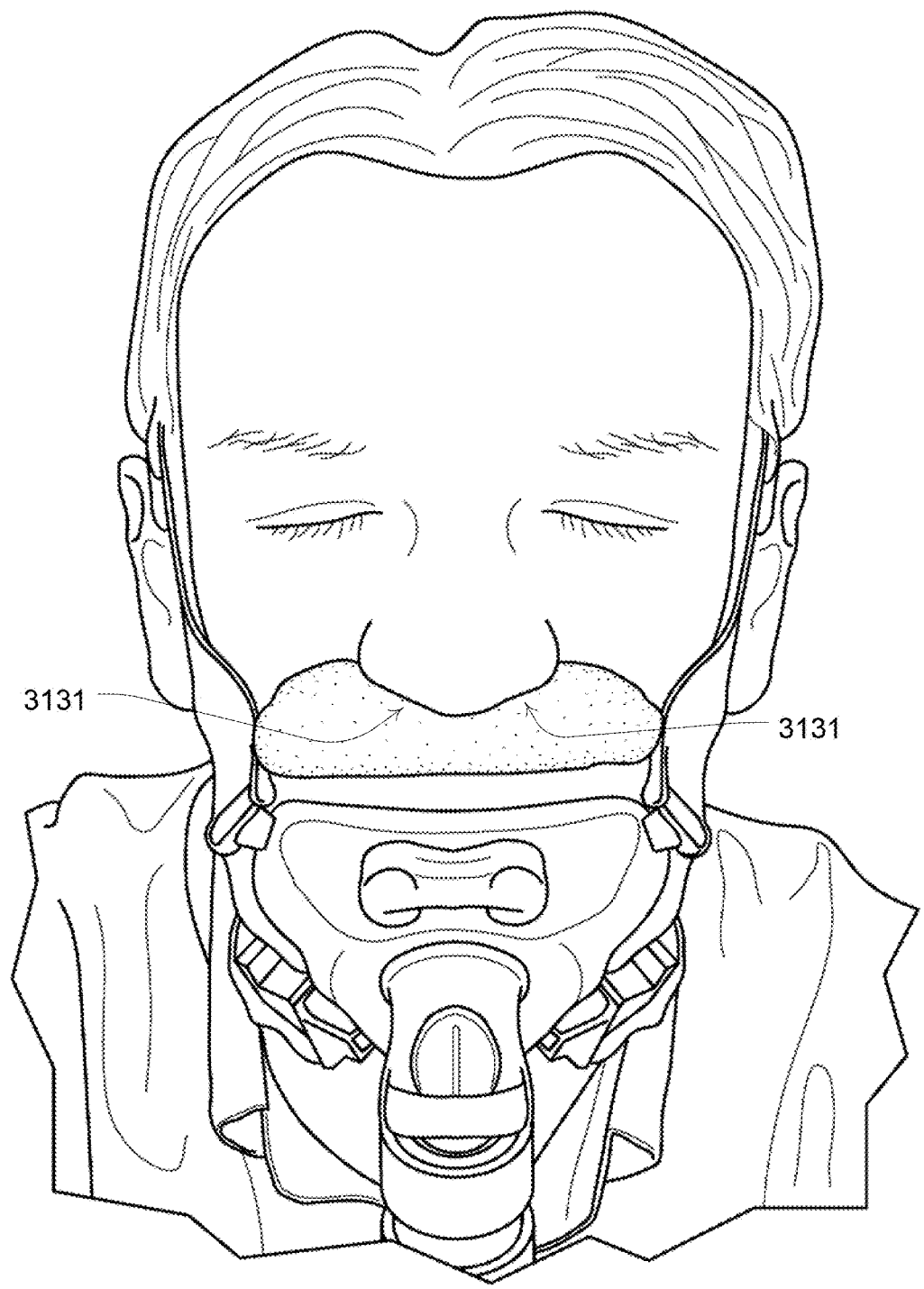
Figure 6:
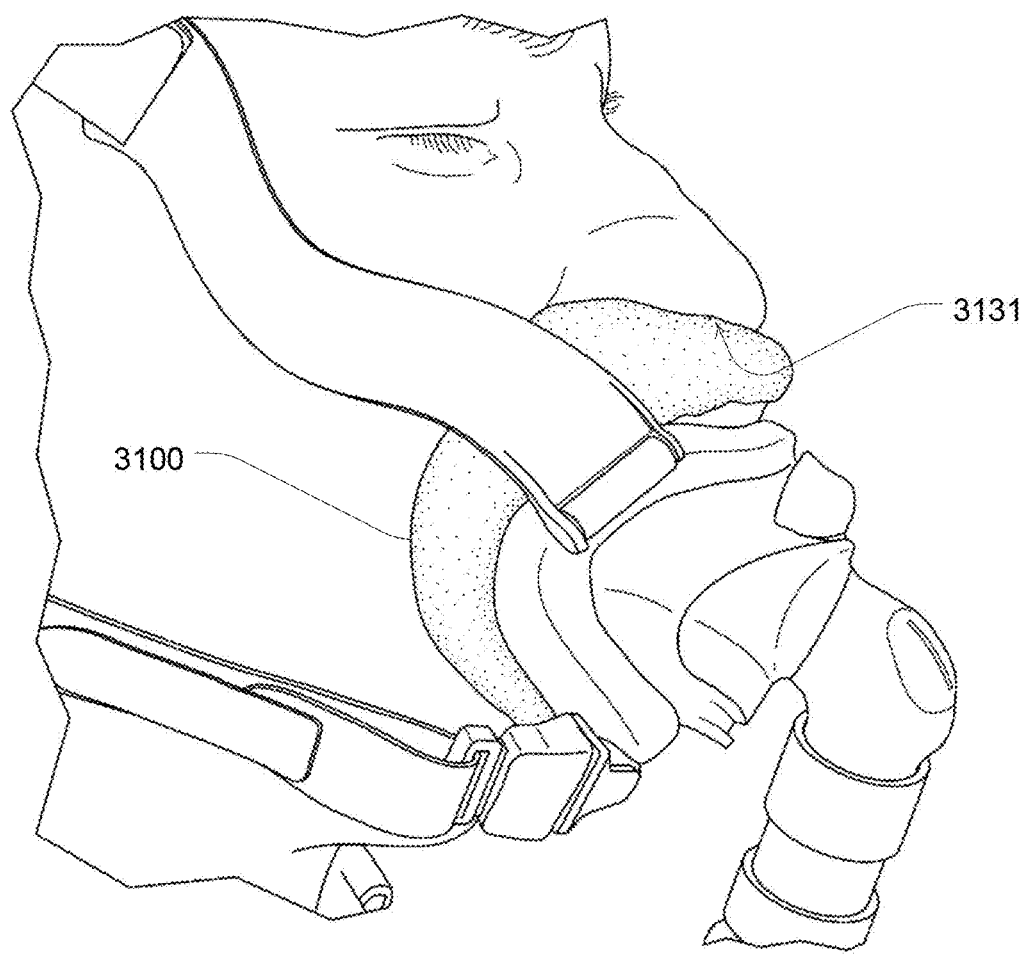
Figure 7:
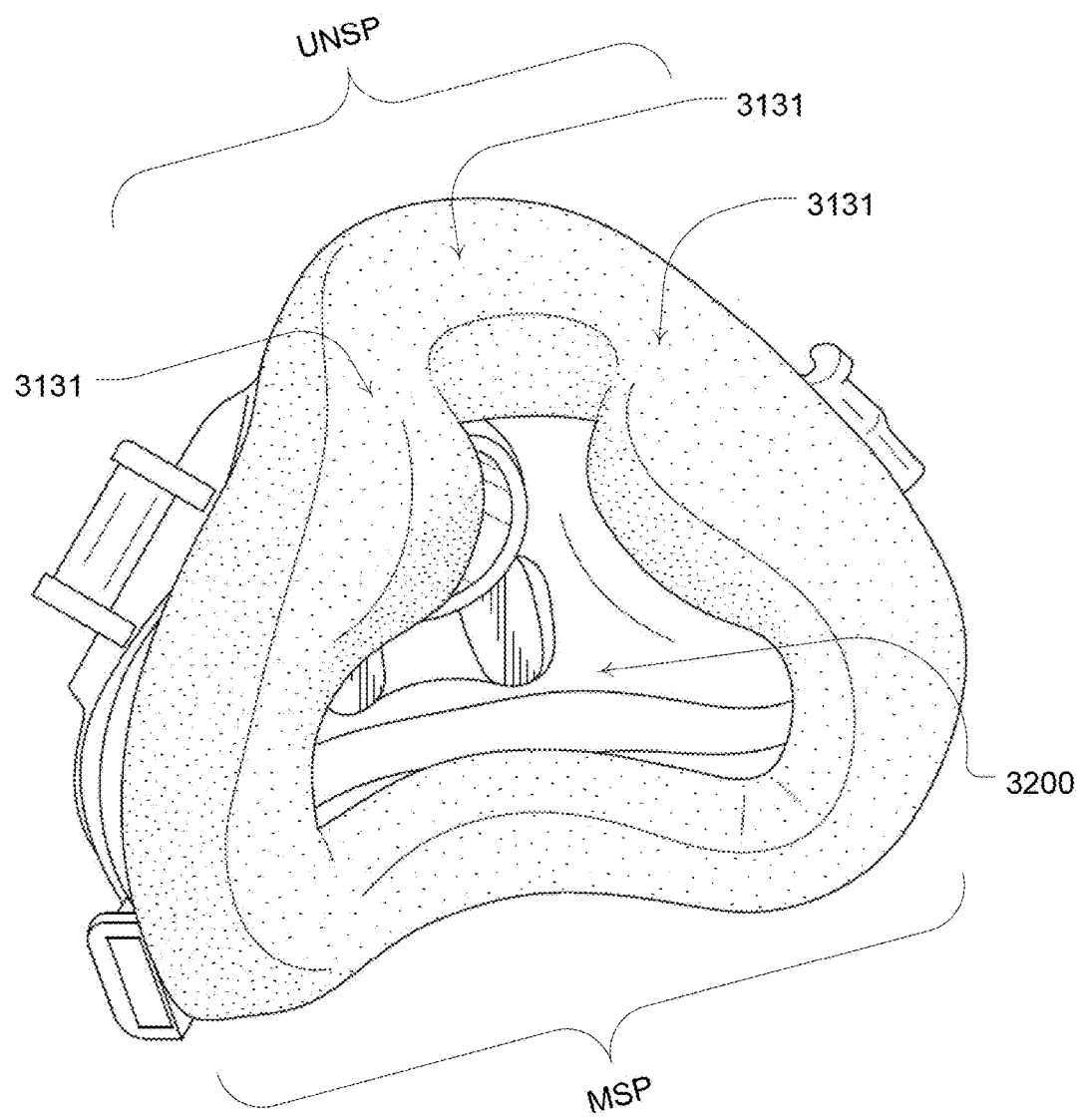
Figure 8:
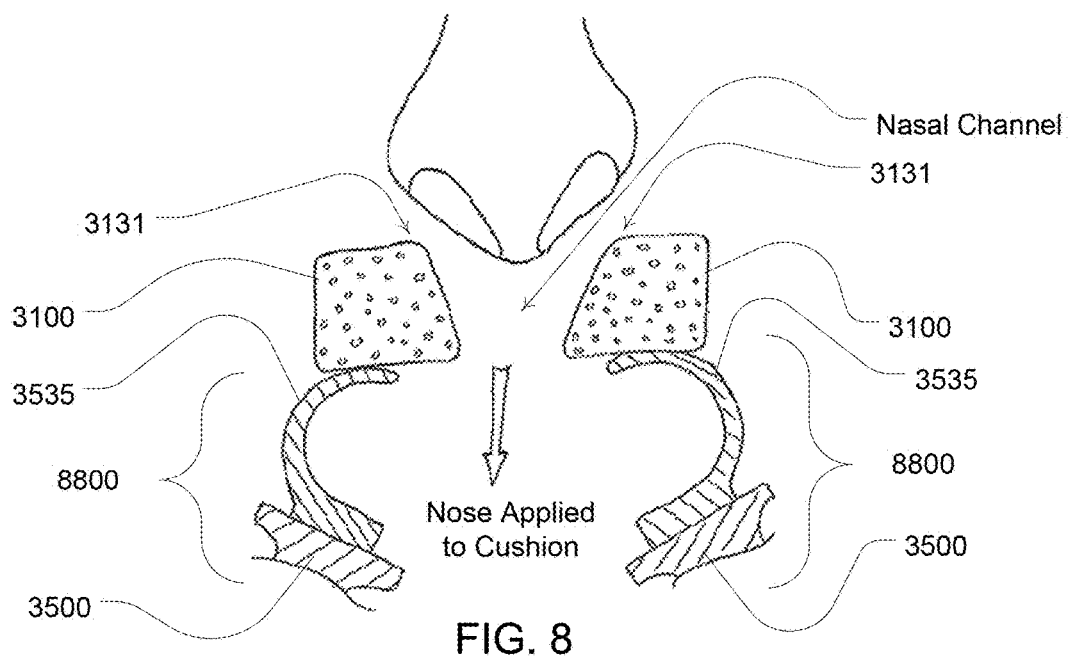
Figure 9:
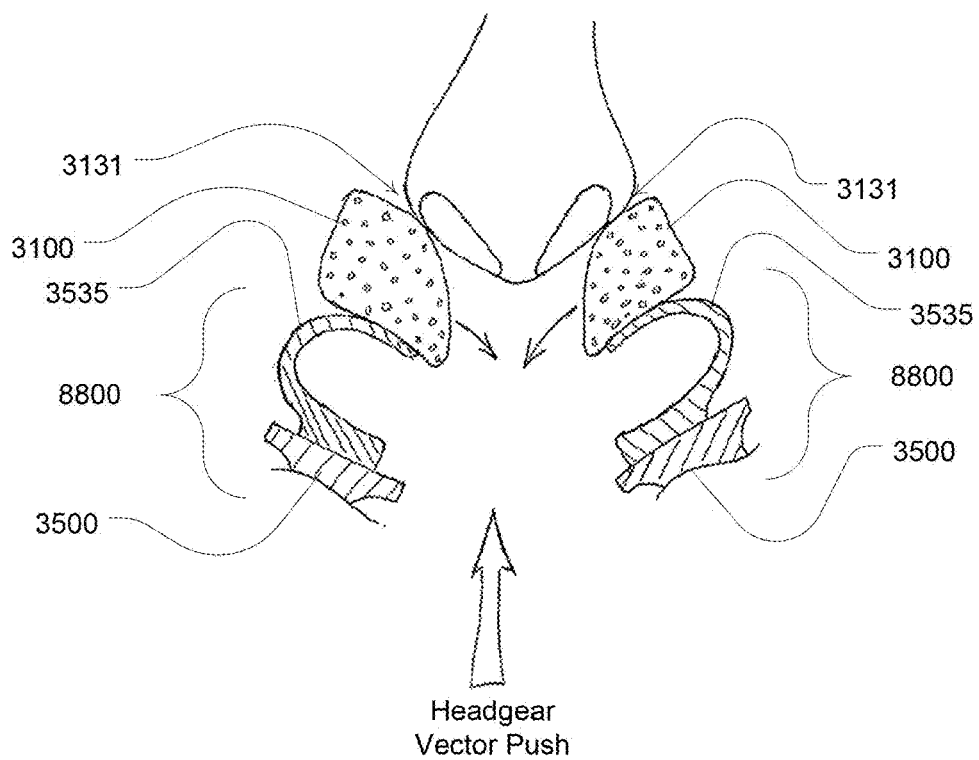
Figure 10:
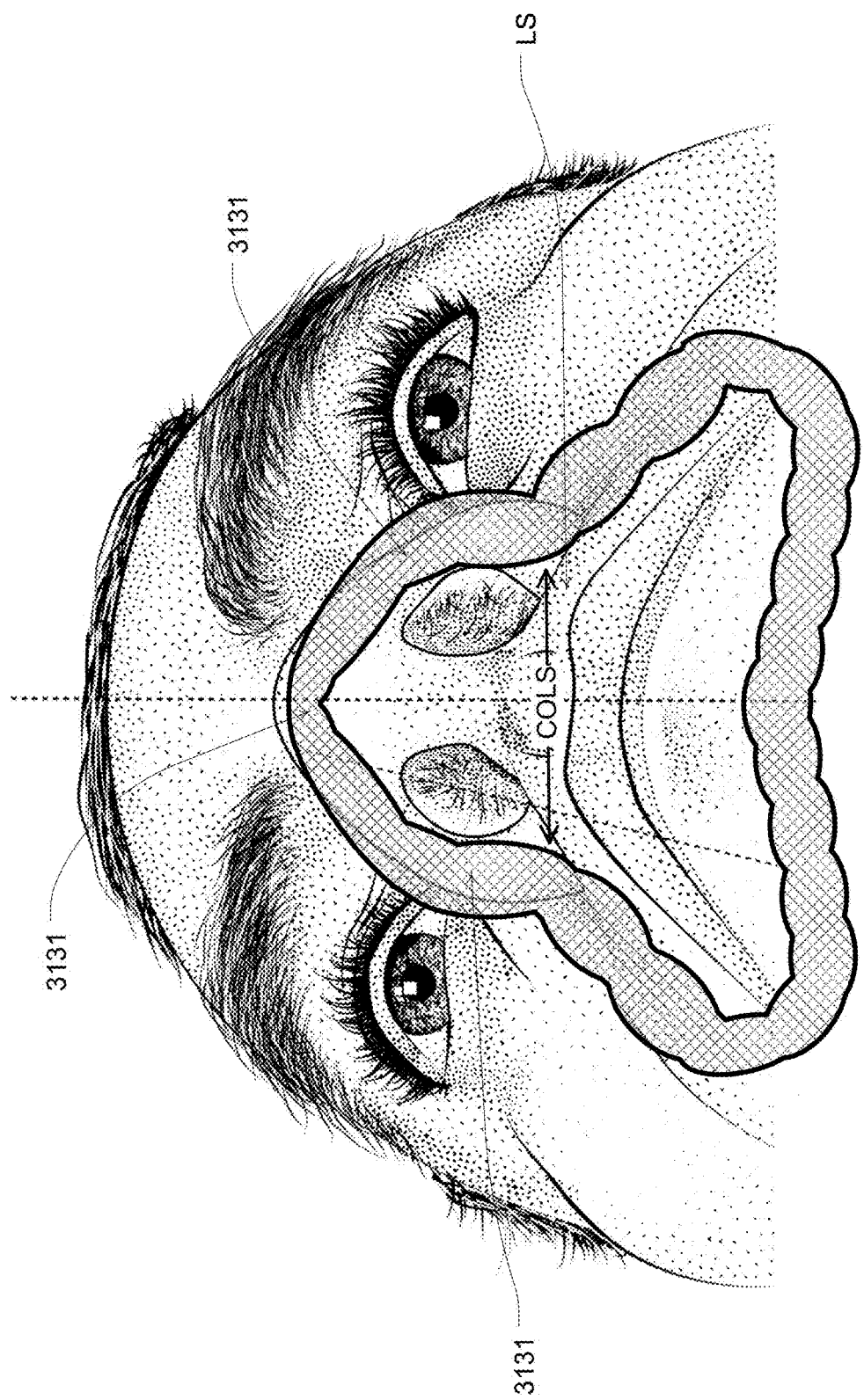
Figure 11:
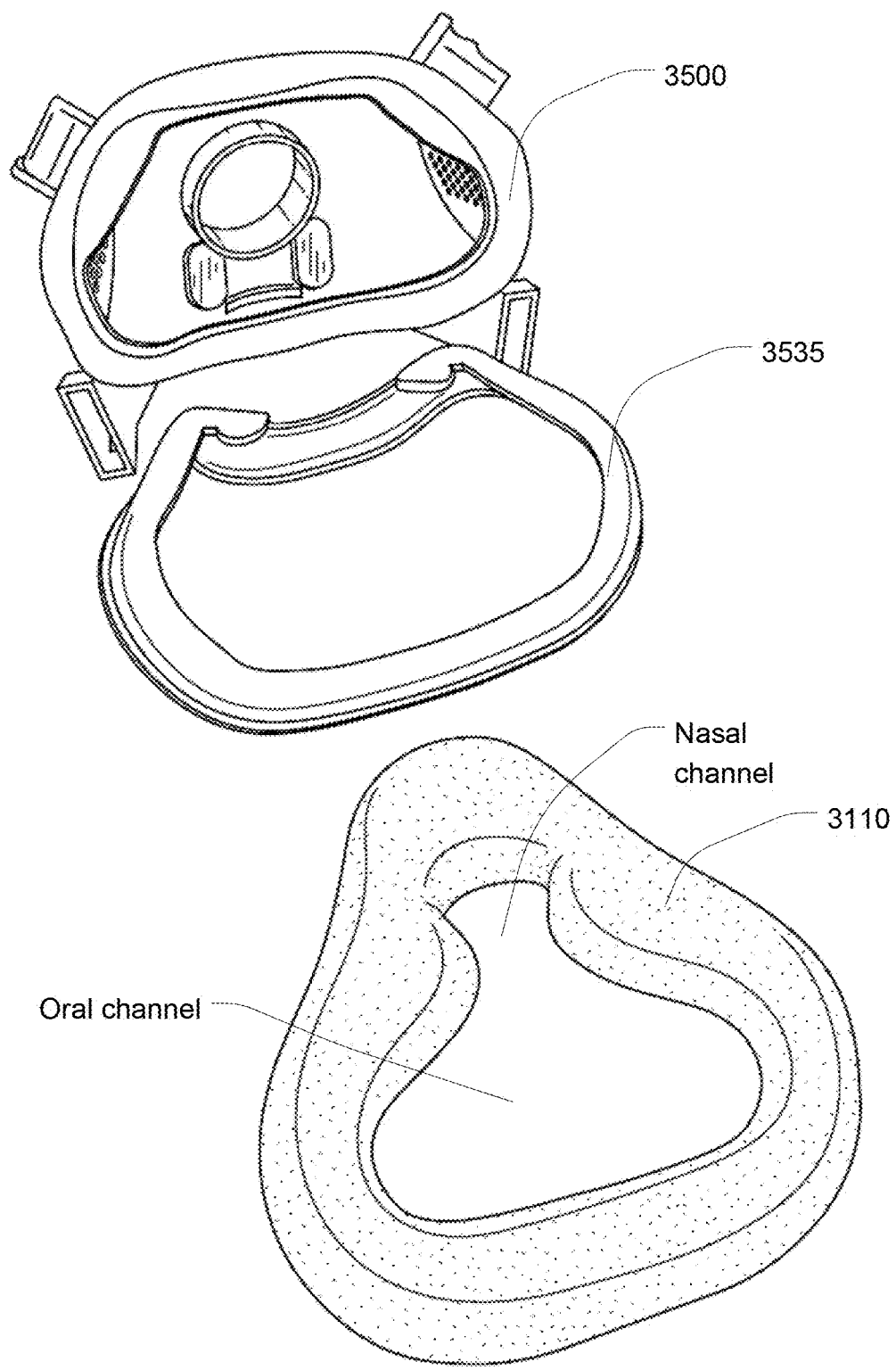
Figure 12:
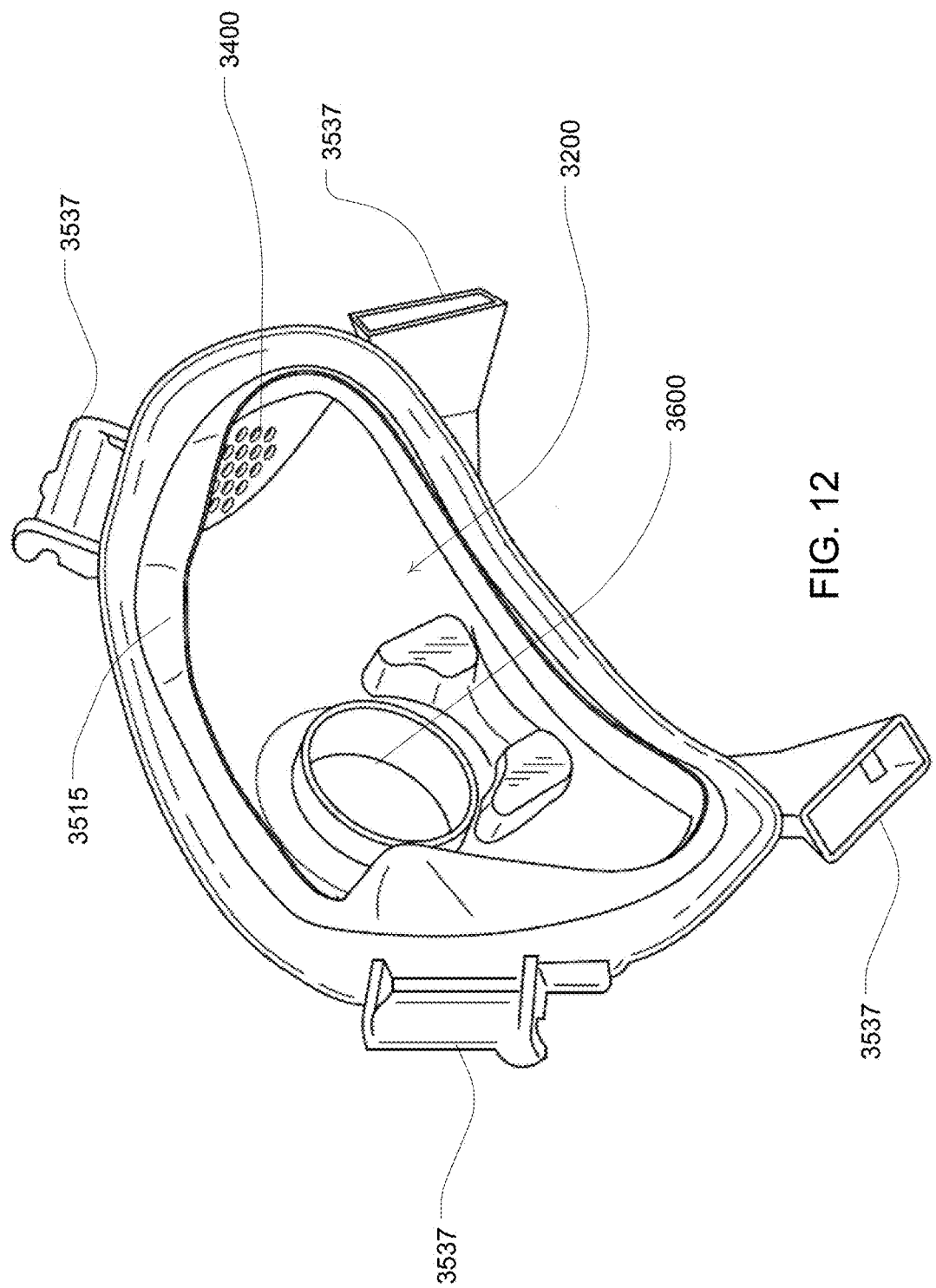
Figure 13:
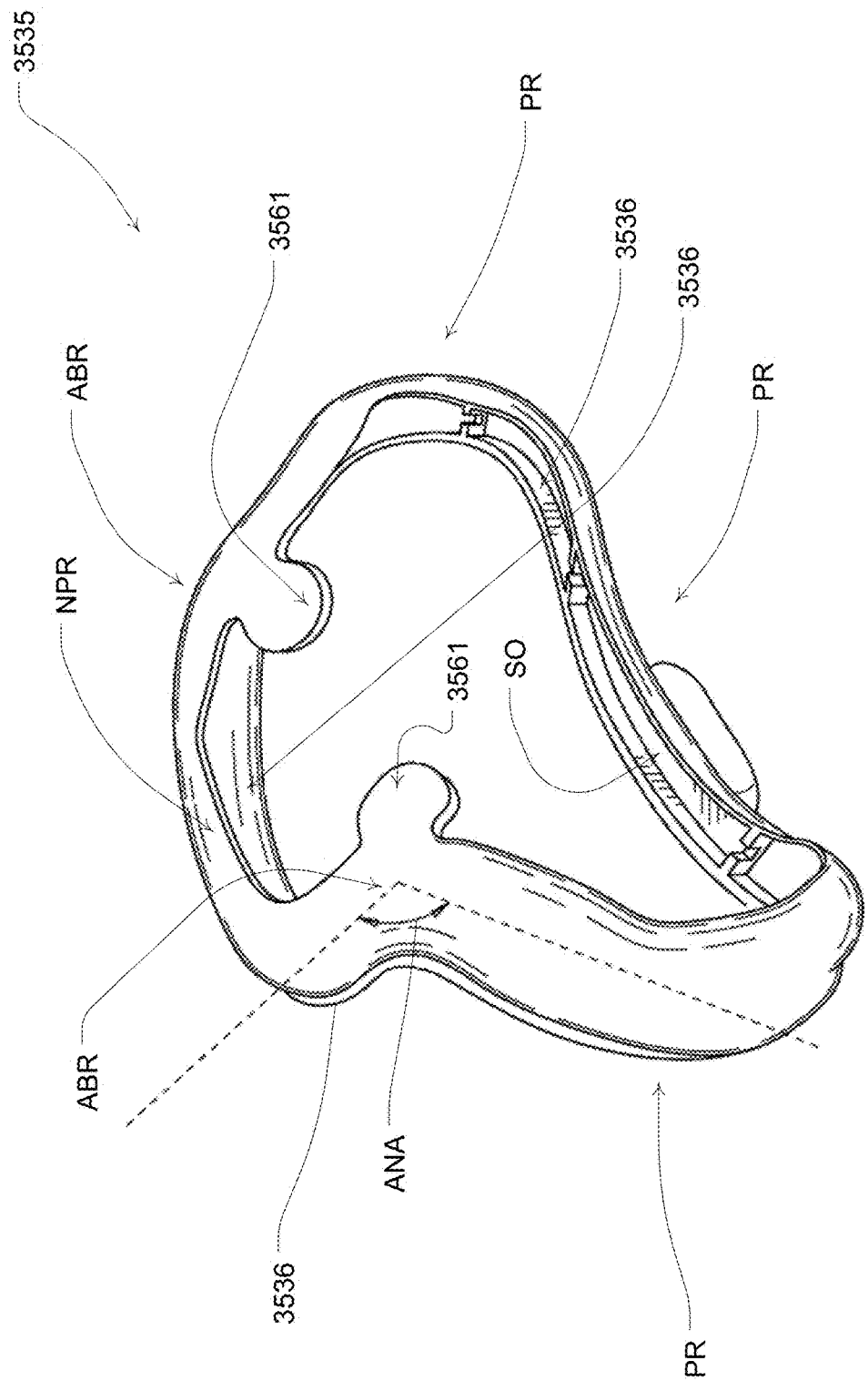
Figure 14:
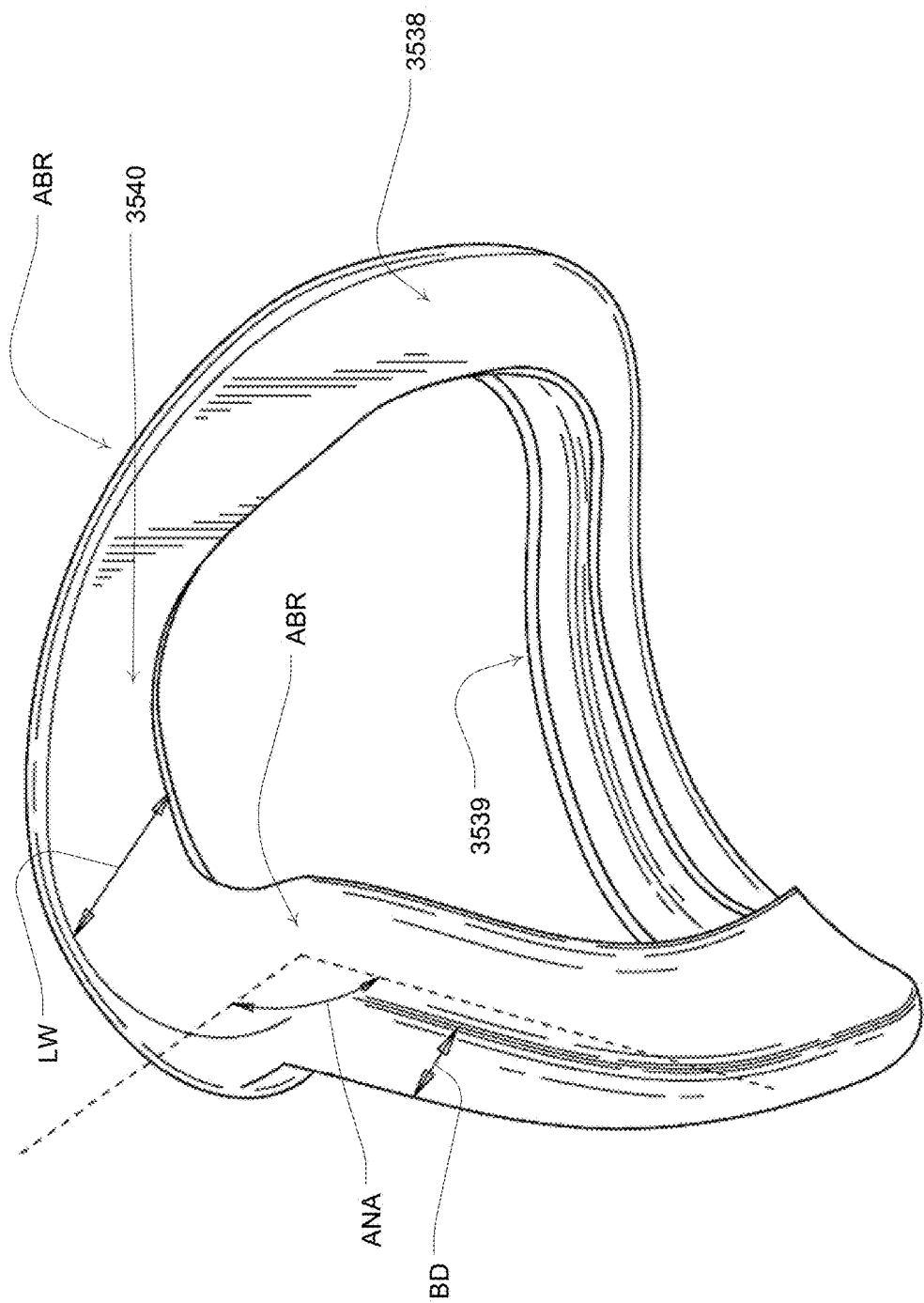
Figure 15:
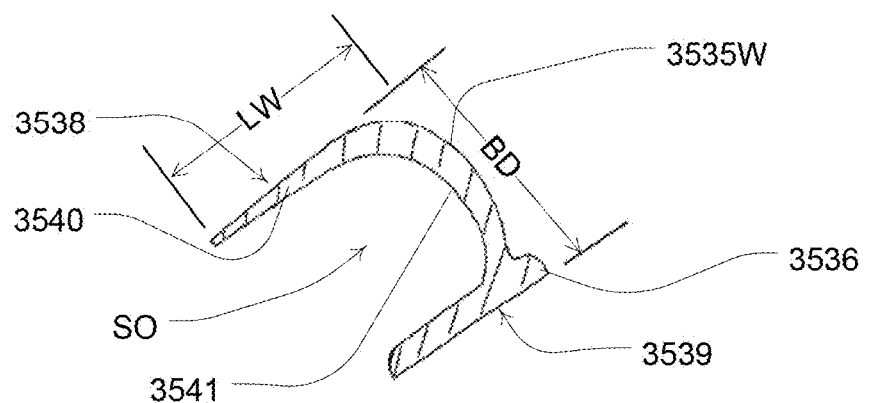
Figure 16:
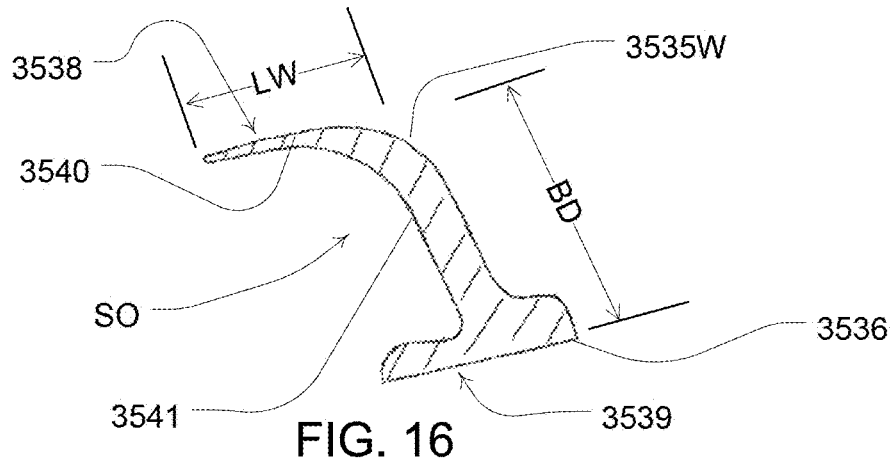
Figure 17:
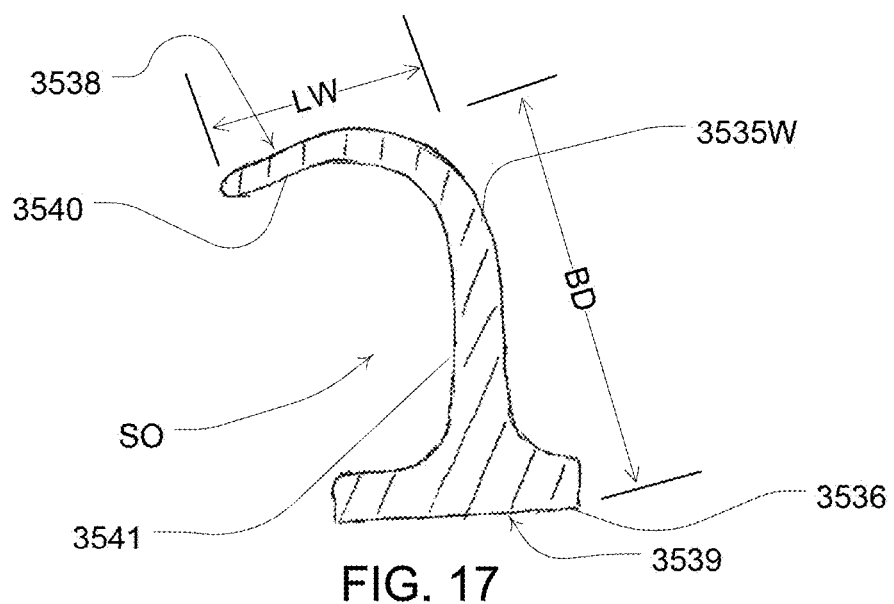
Figure 19:
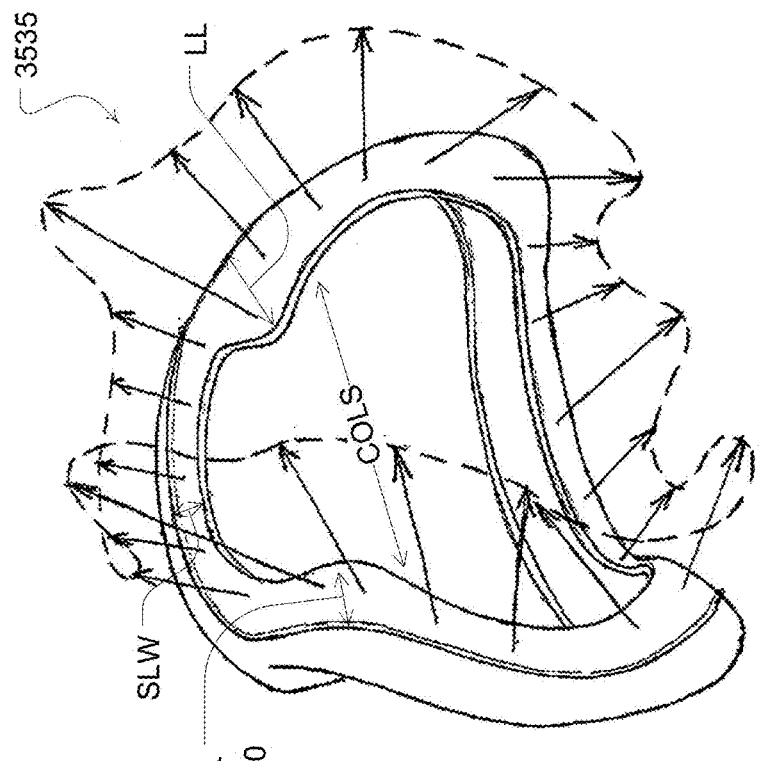
Figure 18:
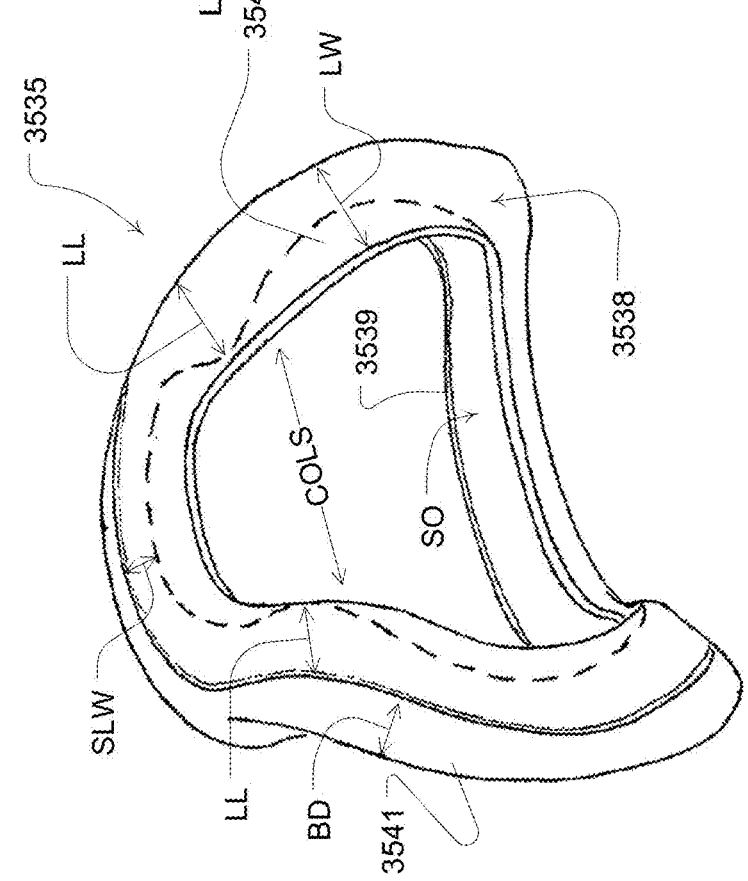
Figure 20:
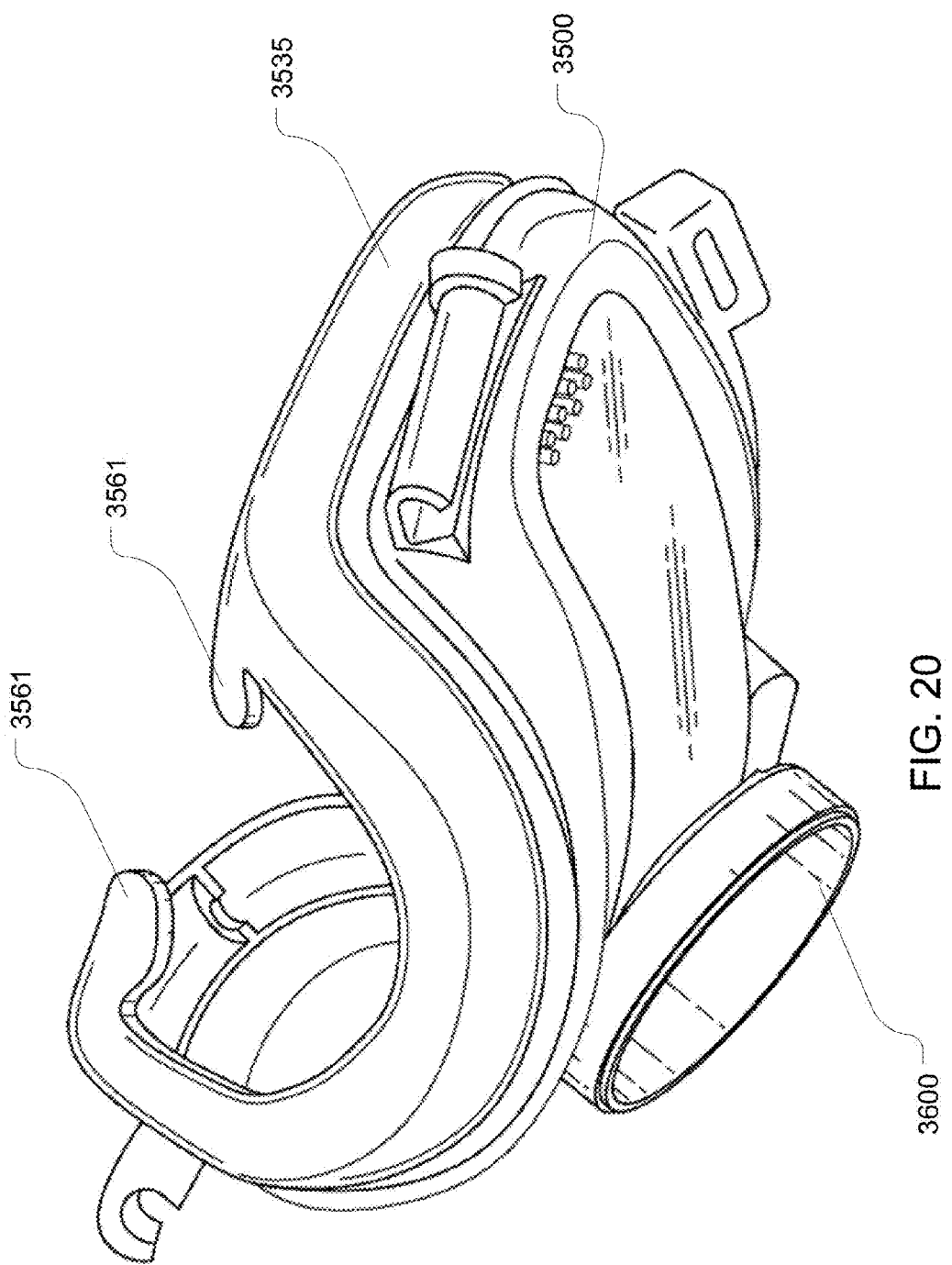
Figure 21:
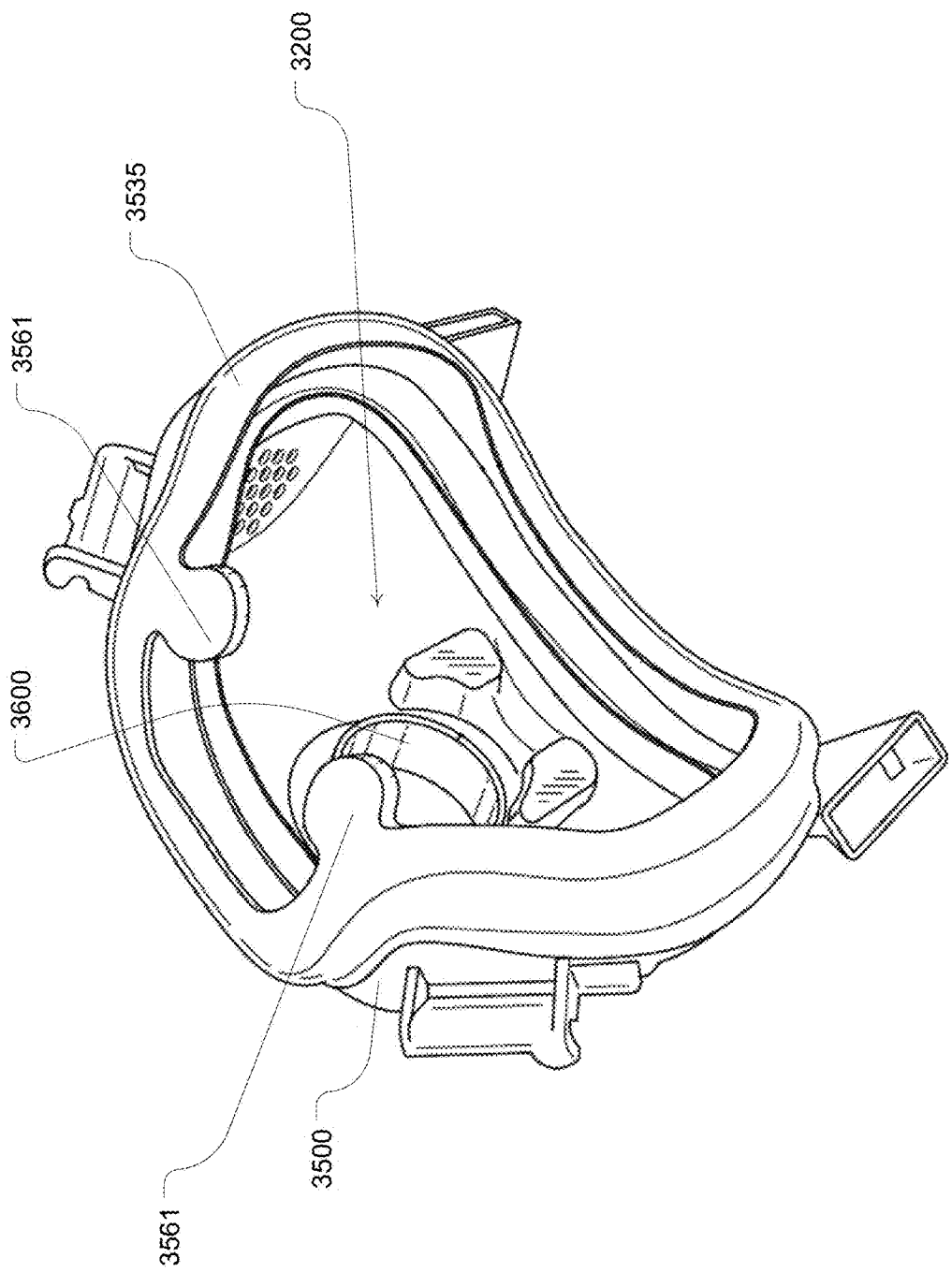
Figure 22:
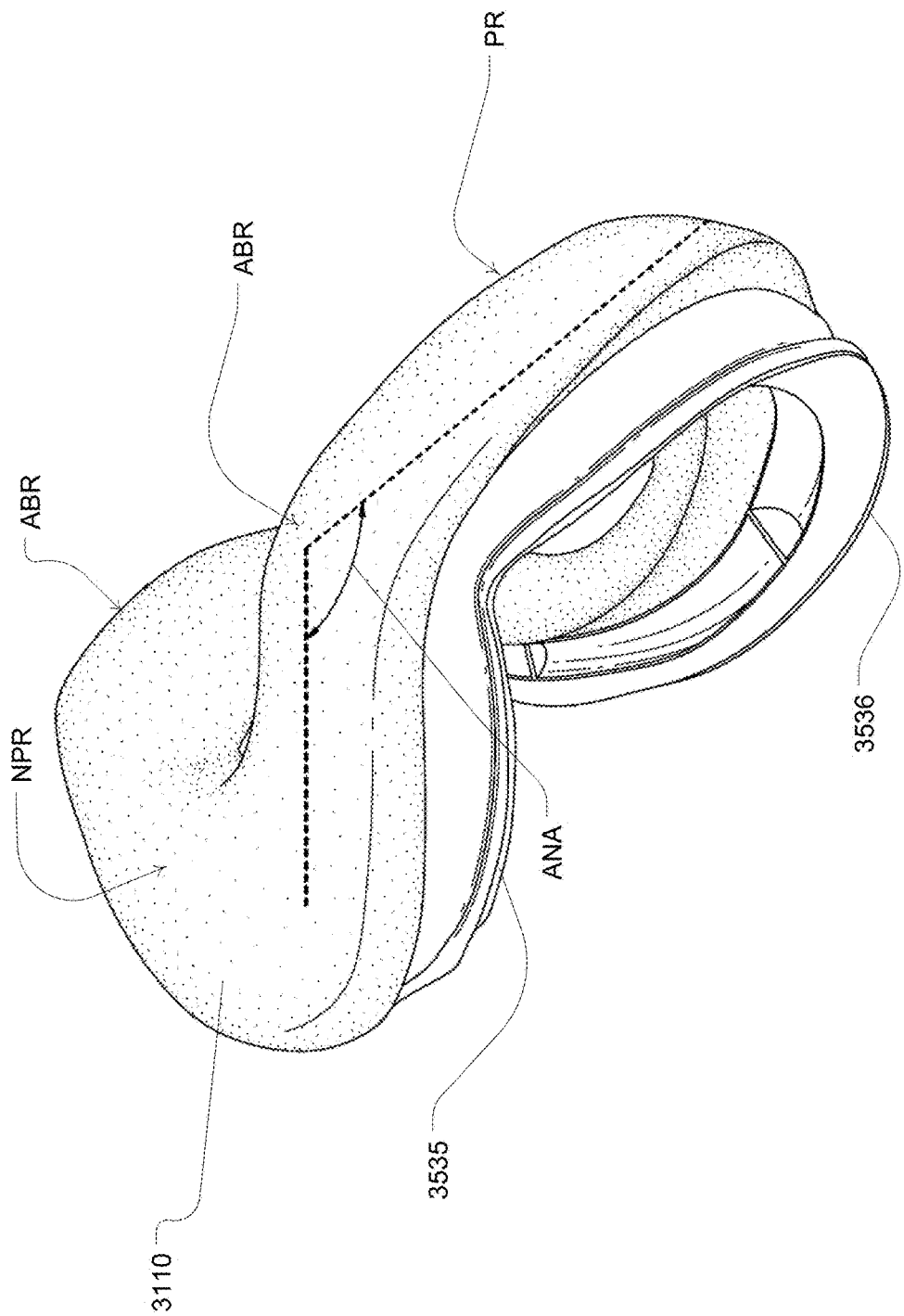
Figure 23:
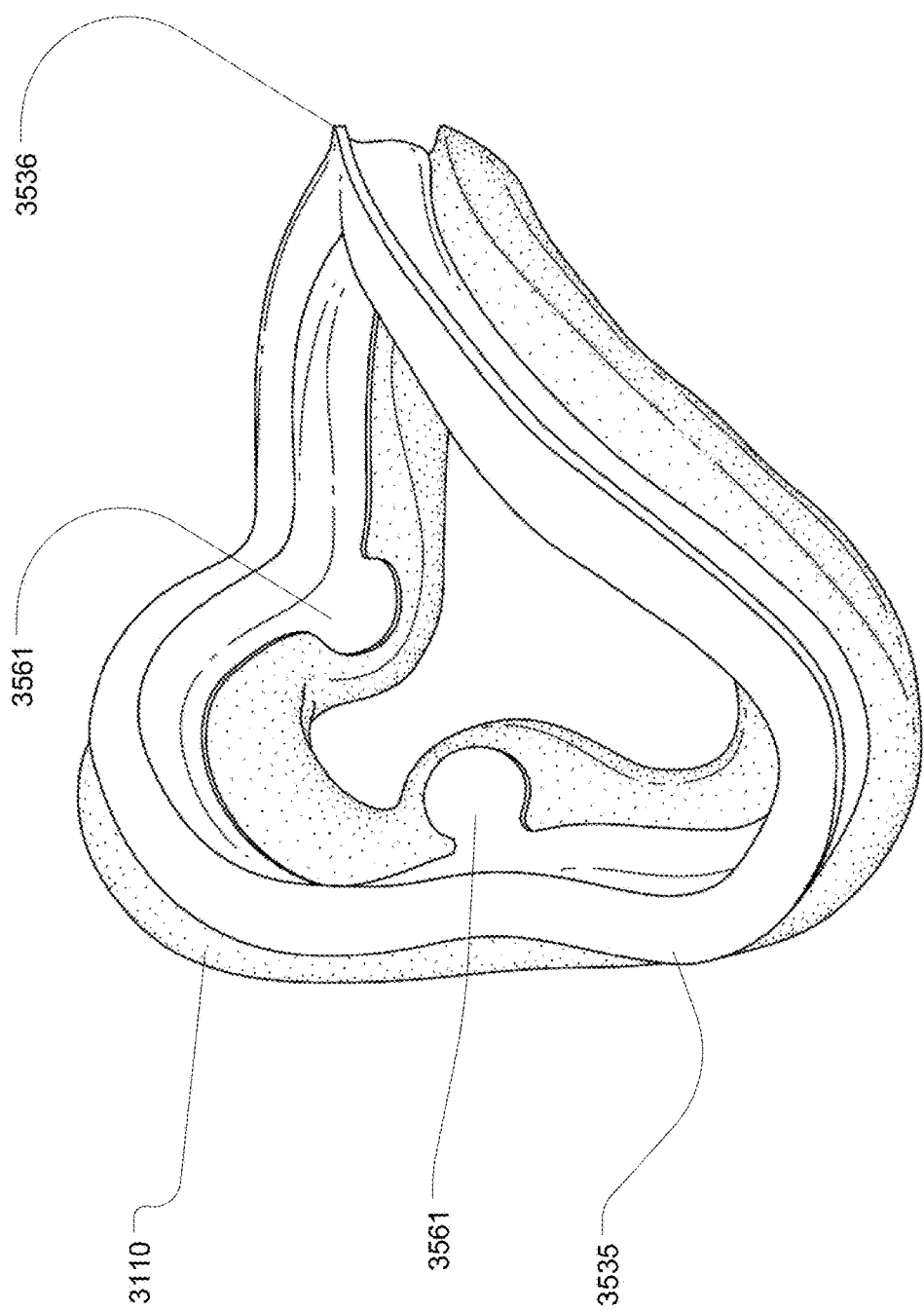
Figure 24:
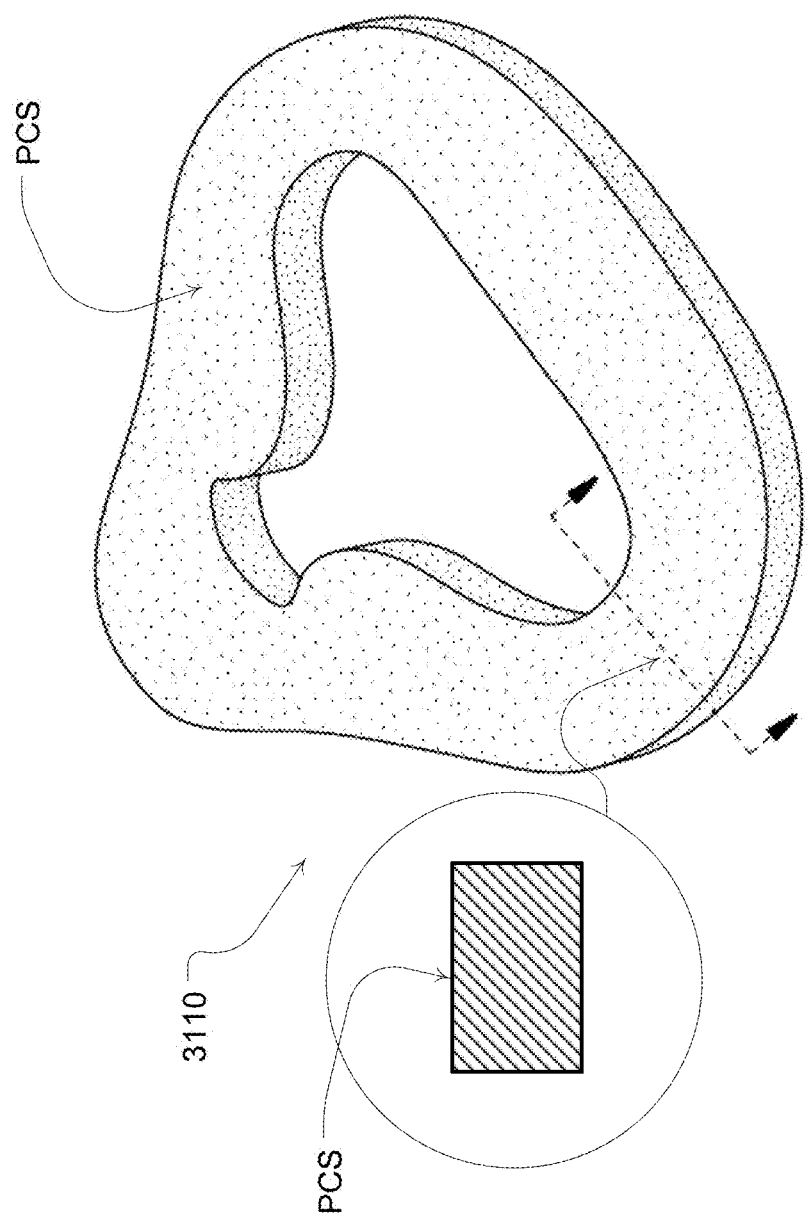
Figure 25:
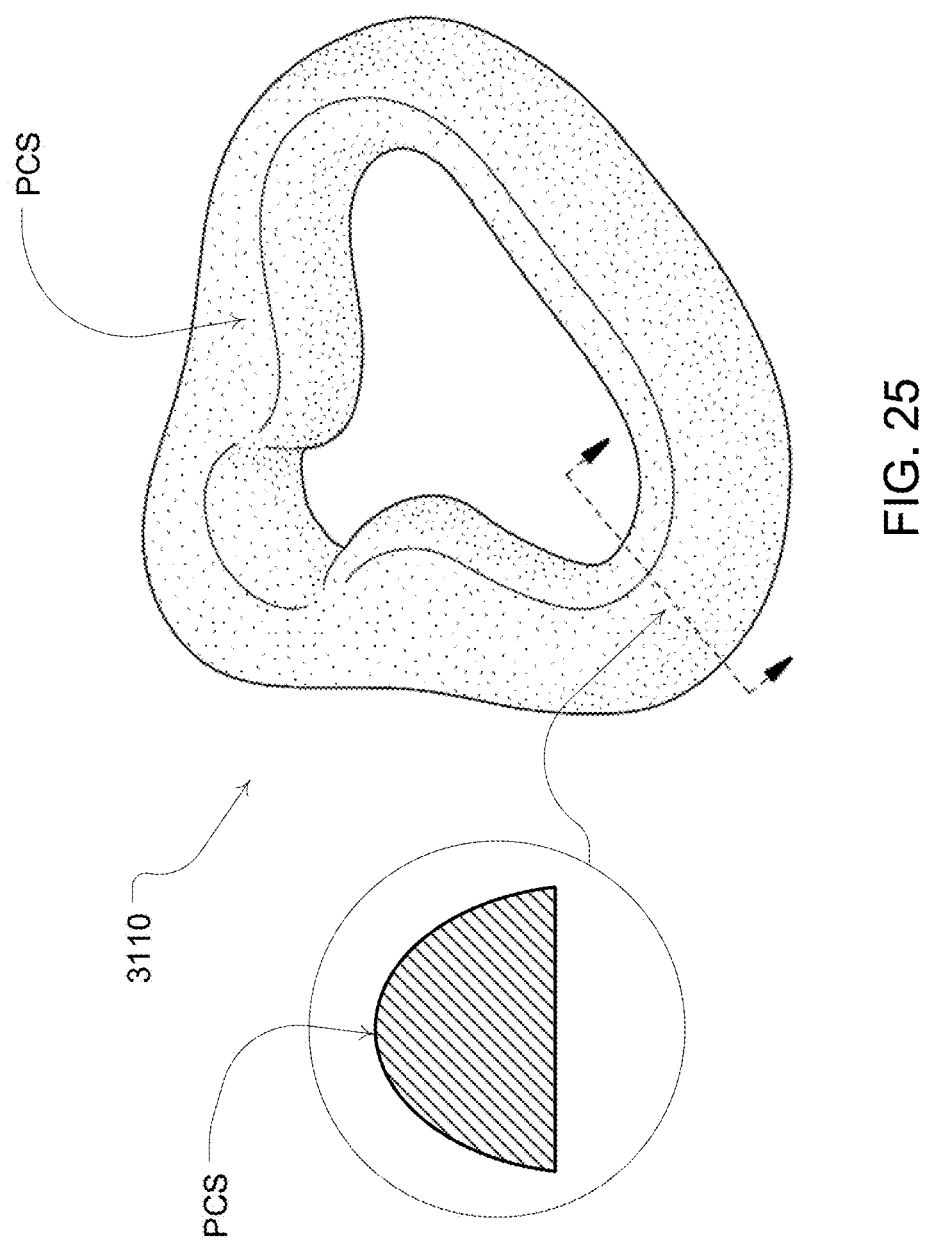
Figure 28:
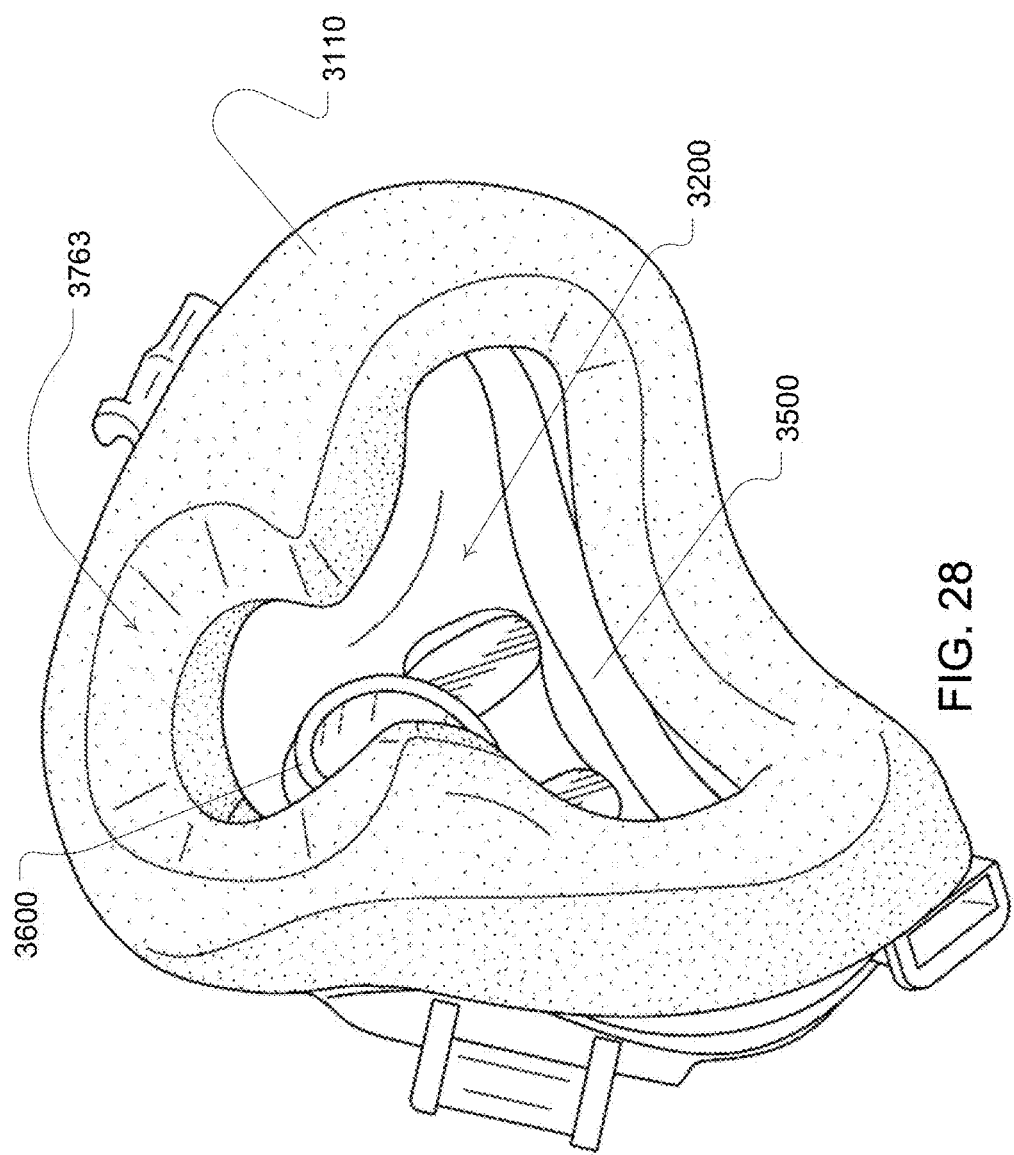
Figure 31:
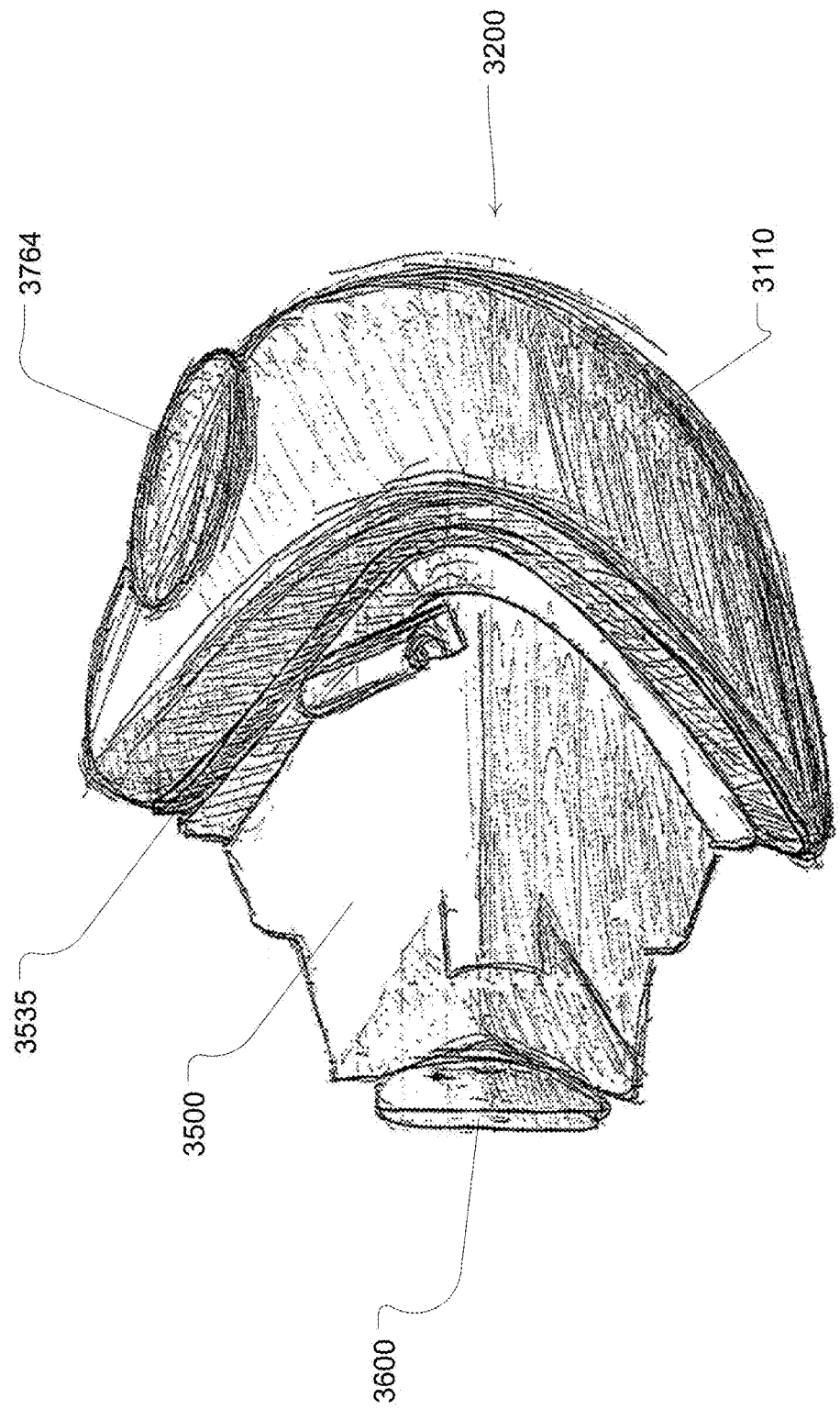

FIGS. 4, 5 and 6 show a patient using an example under the nose patient interface of the present technology;

FIG. 7 is a patient side or proximate view of the cushion of the patient interface of FIG. 4;

FIGS. 8 and 9 are cross sectional views of the patient interface of FIG. 4, particularly showing the nasal channel and nasal region of the patient interface of FIG. 7;

FIG. 10 illustrates facial contact regions of an under the nose mask for some examples of the present technology;

FIG. 11 shows an example frame, cushion support clip and cushion components in some forms of a patient interface of the present technology;

FIG. 12 is an illustration of the example frame component of FIG. 11;

FIG. 13 is an illustration of the example cushion support clip component of FIG. 11;

FIG. 14 is an illustration of another example cushion support clip component;

FIGS. 15, 16 and 17 show cross sectional views of different cushion support regions for some components of the present technology;

FIG. 18 is a further illustration of another example cushion support clip of the present technology;

FIG. 19 illustrations and example force profile that may be achieved with some examples of the present technology;

FIGS. 20 and 21 show a cushion support clip component coupled with a frame component;

FIGS. 22 and 23 illustrates a cushion coupled to a cushion support clip;

FIG. 24 illustrates an example flat contact surface cushion suitable for implementation with some embodiments of the present technology; the figure also includes a callout showing a cross-sectional view of the cushion;

FIG. 25 illustrates an example curved surface cushion suitable for implementation with some embodiments of the present technology; the figure also includes a callout showing a cross-sectional view of the cushion;

FIGS. 26 and 27 illustrate the assembly of the cushions of FIGS. 24 and 25 respectively with a frame;

FIG. 28 illustrates a scalloped nasal region of a cushion in some examples of the present technology;

FIG. 29 illustrates a cushion having left and right nasal support protrusions;

FIGS. 30 and 31 show plan and side views respectively of the cushion of FIG. 29 in a mask assembly of the present technology;

FIGS. 32A and 32B illustrate a further clip and frame connector for some examples of the present technology;

FIGS. 33A and 33B illustrate another clip and frame connector for some examples of the present technology;

FIG. 34 illustrates a still further clip and frame connector for some examples of the present technology; and FIGS. 35A and 35B illustrate yet another clip and frame connector for some examples of the present technology.

DETAILED DESCRIPTION

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

In one form, the present technology comprises apparatus for treating a respiratory disorder. The apparatus may include a flow generator or blower for supplying pressurised respiratory gas, such as air, to the patient 1000 via an air delivery conduit, such as a tube, leading to a patient interface 3000.

Therapy

In one form, the present technology may involve a method for treating a respiratory disorder by applying positive pressure to the entrance of the airways of a patient 1000.

CPAP for OSA

In one example, the present technology may involve a method of treating Obstructive Sleep Apnea in a patient by applying continuous positive airway pressure to the patient with a patient interface described herein. Other positive pressure treatment therapies may also be provided (e.g., bi-level CPAP, etc.)

PAP Device 4000

An example PAP device 4000 in accordance with one aspect of the present technology may include mechanical and pneumatic components 4100, electrical components 4200 and is programmed to execute one or more control methodologies or algorithms. The PAP device may include an external housing 4010, which may be formed in two parts, an upper portion 4012 of the external housing 4010, and a lower portion 4014 of the external housing 4010. In alternative forms, the external housing 4010 may include one or more panel(s) 4015. The PAP device 4000 may include a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may include an inlet air filter 4112, an inlet muffler 4122, a controllable source 4140 of air at positive pressure (preferably a blower 4142), and an outlet muffler 4124. One or more pressure sensors 4272 and flow sensors 4274 may be included in the pneumatic path.

An example pneumatic block 4020 may include a portion of the pneumatic path that is located within the external housing 4010.

The PAP device 4000 may have an electrical power supply 4210, one or more input devices 4220, a processor 4230, a pressure device controller 4240, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The processor 4230 of the PAP device 4000 may be programmed to execute a series of algorithm modules in use, preferably including pre-processing transducer signals module 4310, a therapy engine module 4320, a pressure control module 4340, and further preferably a fault condition module 4350.

Patient Interface 3000

A non-invasive patient interface 3000 in accordance with one example of the present technology may be considered with reference to FIGS. 4-7. The patient interface may include any of the following features: a seal-forming structure 3100, such as a cushion 3110, a plenum chamber 3200, a positioning and stabilising structure 3300 and a connection port 3600 for connection to an air/gas circuit 4170. In some forms, one or more such features may be provided by one or more physical components. In some forms, one physical component may provide one or more functional features. In use, the seal-forming structure 3100 may be arranged to surround an entrance to the airways of the patient so as to facilitate the supply of air at positive pressure to the airways.

For example, as shown in FIGS. 4-7, the patient interface may be configured as a mask to provide a sealed interface with the mouth and nares of a patient so as to direct a breathable gas under pressure to both the mouth and nares. Such a mask may be configured to be a substantially under-the-nose mask. As illustrated, the plenum chamber 3200 may be formed by a frame 3500 and cushion 3110. The cushion 3110 may also serve as the seal forming structure 3100. The frame may be adapted for coupling with a respiratory treatment apparatus so as to permit communication of a pressurized gas to a respiratory system of a patient from the respiratory treatment apparatus. The cushion may then be adapted to couple with the frame.

In some cases, as illustrated in FIG. 7, the cushion may form a seal with a substantially under nose seal portion UNSP and a mouth seal portion MSP. Such a configuration may be considered in reference to the illustration of FIG. 10. The under nose seal portion may be formed by a sub-nasal ridge 3131 that forms a semi-peripheral sealing boundary about both nares of the patient. In this regard, such a seal may be achieved with both nares and the mouth while in some cases avoiding a seal portion or other mask contact structure at a central region of the lip superior LS. Such a mask may provide a more open and comfortable feel for users such as when compared to mouth masks that may be combined with nasal prongs, while still providing an effective seal.

Obtaining a seal with a single cushion that seals both over the mouth and under the nares of the nose can be difficult to achieve with a nasal cradle design that uses standard silicone cushion materials. It has been discovered that the anthropometrical variations of facial features are large. Some materials, such as standard silicone, may have insufficient flex to achieve both seal and comfort, especially with respect to the intricate facial features surrounding the nose and the mouth.

In some cases, this problem may be overcome by an implementation of foam, such as an open cell foam. In some examples, the cushion may be a foamed silicone material or a polyurethane foam, etc. In some cases, a very low durometer thermoplastic elastomers (TPE), thermoplastic polyurethane (TPU), thermoplastic polyurethane (TPV), silicone or rubber material might be implemented. The compliant nature of foam allows it to, under relatively small tension force, compress into intricate facial features and affect a good seal. This, combined with the easy adaptability and softness experienced by the patient, provides for a relative fast and easy mask set-up. The porosity of the foam also exhibits better breathability than silicone and may permit wicking away of moisture from the face. Thus, the use of foam may be associated with better cooling and reduced discomfort in the areas of contact or sealing.

In some cases, the cushion and/or frame may define a single chamber, such as the plenum chamber 3200 that is illustrated in FIG. 7, which covers the patient's mouth and the nares of the nose from underneath. As discussed in more detail herein, the cushion may have a substantially oval and/or triangular shape. The sealing surface may continuously extend substantially in two plains—one plane that allows it to seal with the mouth and a second plane that facilitates the seal under the patient's nostrils. The second plane may form an angle with respect to the first plane. The angle may be approximately close to ninety degrees or approximately perpendicular, but may be slightly larger or slightly smaller. Such an angle may approximate the nasolabial angle. Such a single chamber foam cushion may be designed to attach to a frame directly or by way of a clip as discussed in more detail herein.

The seal around the mouth and the nares of such a mask can be produced through the interaction between the patient's face and the combined reaction of the assembly (e.g., frame, flexible clip, and/or cushion) and subject to tension from headgear. The structures of the components when assembled can work together to provide variable amounts of compression around the nose and mouth so that an effective seal is produced in these areas.

FIGS. 8 and 9 show a cross sectional view of a sub-nasal region of a portion of the seal including an example sub-nasal ridge 3131. The figures illustrate a mechanism for achieving the seal in the sub-nasal region.

When the nose is applied onto the cushion (e.g., foam) in the region of the sub-nasal ridge, the headgear may be tightened. The headgear vectors help to enforce a seal at the periphery of both of the nares through the combination of the cushion (e.g., foam) and/or the cushion support structure 8800 (e.g., clip 3535) rolling inwards (illustrated by arrows RR in FIG. 9) and closing around the periphery of the nares. The flexibility of the combination of cushion and/or cushion support structure can enable the cushion to align to the alar angle and to the Nasolabial angle of the nose. As the headgear vectors are further tightened, a greater sealing force can be applied to the periphery of the nares. The reaction forces in the cushion and the cushion support (e.g., clip and/or frame), caused by the rolling and compression of them, result in a reaction vector that radiates (approximately perpendicularly) from the frame support back towards the patient. Moreover, the generated gas pressure (e.g., from a flow generator coupled to the mask assembly) that accumulates inside the mask chamber can push the cushion (e.g., foam) outwards. This can ensure an opening up of the air passage to the nostrils and may also compress the cushion upwardly (towards the patient's sub-nasal region), thus generating sealing pressure around the nares.

In some cases, there may be a potential for occlusion of the nares by some cushions during set-up or use. When the seal around the nares is associated with the compression of some foams, it can lead to nasal occlusion occurring at mask set-up before pressure is applied to the mask. In order to minimize the potential for occlusion, a balance can be attained between the foam thickness, the foam profile around the periphery of the nares and cantilever spring characteristics of the support structure (e.g., clip if used).

In the case of implementation of foam, a thin foam section, such as in the nasal region may be suitable. For example, a foam thickness of about 8 to 20 mm (e.g., 13 mm) may noticeably improve/prevent set-up occlusion. In some cases, the foam internal profile may be aligned and/or shaped to match the nares opening such as at their periphery. A soft elastic material (such as silicone, TPE, TPU etc.) may be implemented as a material such as for the cushion support. Such a material can be configured to pass on a light cantilever spring affect onto the nose.

During a pressure treatment, such as a CPAP treatment, occlusion may be avoided at the nares. The internal profile (as illustrated in FIG. 9) of the foam cushion can provide relief around the nares. Generally, the foam may be compressed around the periphery of the nares by the internal CPAP pressure inflating the nostrils. In order to achieve a suitable and comfortable seal, the foam rigidity should be no greater than the reaction force generated by the internal CPAP pressure inflating the nostrils. This situation can hold the nares open during CPAP and no occlusion will result.

The cantilever spring force of the cushion support (e.g., clip and/or frame) can be soft enough to allow the nose to press into the foam cushion at set-up without occluding the nares. Conversely, the spring force of the cushion support can provide enough reaction force to press the foam cushion into all the sealing zones of the mask. This may be significant for areas such as at the corners of the nose.

Example components for a mask assembly of the present technology are further illustrated in FIGS. 11 through 23. In some cases, as shown in FIG. 11, the frame 3500 may be a separable component from the clip 3535 and the cushion. As seen in FIG. 12, the frame may include a set of fasteners 3537. The fasteners may be employed for connection of head gear (not shown) to position and support the mask assembly for use. The frame may also optionally, include a vent 3400. In one form, the vent 3400 may be constructed and arranged to allow for the washout of exhaled carbon dioxide. The vent 3400 may be formed by a plurality of holes, for example, about 20 to about 80 holes, or about 40 to about 60 holes, or about 45 to about 55 holes. The vent 3400 may be located in the plenum chamber 3200. Alternatively, the vent 3400 may be located in a decoupling structure, e.g. a swivel or other coupler.

The frame may typically include a connection port 3600. The connection port 3600 allows for connection to an air circuit 4170, such as for a connection with a respiratory treatment apparatus or flow generator. Such a connection to an air circuit may be by way of a decoupling structure as previously mentioned. In some cases, the patient interface 3000 may include an anti-asphyxia valve (not shown). Optionally, the frame may include one or more additional ports. Such additional ports may permit access to the volume within the plenum chamber 3200. For example, such a port may permit introduction of a supply of supplemental oxygen. Such a port may also serve as a coupler or housing for a sensor for direct measurement of a property of the gases within the plenum chamber 3200, such as pressure.

The frame may contain a flange 3515 around its rear (patient proximate side) periphery such as the one illustrated in FIG. 12. This flange may vary in angle and width around the periphery of the plenum chamber in order to follow the curvature of the sections of the face where a seal is to take place. The flange may extend generally parallel to those areas near where the seal is to exist on the patient's face. A varying angled flange can work together with the headgear vectors to impart a desired amount of cushion compression to the varying parts around the mouth and the nares to achieve a comfortable and effective seal.

In some cases, the mask assembly may employ a clip 3535 as illustrated in FIG. 13 or FIG. 14. The clip may be releasably attachable with the frame so as to permit a convenient replacement of the cushion that may be applied to the clip. In this regard, FIGS. 20 and 21 illustrate the clip (without a cushion) coupled to the frame. However, any one or more of the features of the clip described herein may optionally be integrated with the structure of the frame itself and the cushion applied thereto.

In some cases, the clip's profile can assist in imparting form to the cushion so as to configure the cushion into its multi-dimensional shape (e.g., multi-plane) suitable for conforming to the person's face so as to form a good seal in an under-the-nose configuration. In this regard, as seen in FIGS. 13 and 14, the clip may be formed with a bend or angled region ABR. The angled region ABR permits an angle between a nasal plateau region NPR and a mouth periphery region PR. An approximately nasolabial angle ANA may be formed by a plane of the mouth periphery region and a plane of the nasal plateau region. When the cushion is applied to the clip (and/or frame) such as shown in FIGS. 22 and 23, the characteristics of these regions may be imparted to the cushion in the case that the cushion is not already formed with such regions.

Alternatively, a 2D flat clip may be used. In this case the 3D shape is imparted to the clip/cushion combination by attachment onto a 3-D shaped frame.

Generally, the clip may be permanently coupled to the frame or include connectors 3536, such as those illustrated in FIGS. 13, 22 and 23, to facilitate its removable coupling with the frame. These elements may be formed around one side (e.g., the lower periphery or distal side) of the clip where it interfaces with the frame. Additional examples of such connection elements are explained in more detail herein with reference to FIGS. 32-35. The clip's opposing side (e.g., upper peripheral surface or patient proximate side) provides a connection or landing surface for attachment of the cushion (e.g., the foam ring). In this regard, the features of the clip may serve as a suspension for the cushion.

The clip's periphery may differ in different sections of the clip so as to provide different regions of flexibility/rigidity to the cushion. Examples may be considered with reference to the cross sectional views of FIGS. 15, 16 and 17. For example, the clip may be formed so as to have an open or concave wall 3535W with a cross-section along the clip's periphery that may vary in geometric shape. These cross-sectional shapes may be, for example, formed as a U-shape such as that shown in FIG. 15, an L-shape such as that shown in FIG. 16, or a C-shape such as that shown in FIG. 17. Other examples may include I-shape or Z-shape cross sectional configurations. In some cases it may be formed with some or all of these wall formations. The opening of each shape (shown in FIGS. 13, 15, 16 and 17 with reference character SO) being directed inwardly towards the center or plenum chamber of the mask. These different wall structures may have different flexibility characteristics. Such cross-sectional shape(s) can enable the clip to act as a spring or cantilever-type spring. Such a spring configuration can permit the foam cushion to further conform to the face and compress towards it once alignment has been achieved, improving cushion compliance to the face.

Accordingly, the clip (or frame) may be formed with a flexible peripheral lip that variably supports the foam cushion. Pressure within the chamber formed between the mask frame, clip, cushion and the face of the patient, acts on the inside of the clip section (e.g., the shape opening SO of the wall) and cushion and pushes the peripheral lip and the cushion towards the patient's face, thereby reinforcing the seal created by the cushion. As pressure increases, so does the force creating the seal. As such, the wall of the clip may also be chosen to have thickness and flexibility to allow the air pressure to create an air spring effect, further contributing to the compliance of the seal.

As previously mentioned, the wall geometry around the periphery of the clip may vary in order to alter the stiffness or flexibility around the nose and mouth sealing regions. Different stiffness/rigidity may be achieved in these different sections of the face to achieve a balance between good seal, comfort and stability. For example, around the nose, a softer seal can be achieved as the nose is sensitive to pressure, whereas the sides of the mouth can withstand larger sealing pressures without discomfort. Thus, the flexibility of the clip (or frame) may impart these different flexibility characteristics.

In some such examples, support for the cushion in the nasal sealing area may be formed as the flexible cross-section "U" geometry illustrated in FIG. 15. The clip wall 3535W may then have a cushion support surface 3538 and a frame coupling surface 3539 for a connector as discussed herein. In some cases, support for the cushion in the sealing area at the sides of the mouth may be formed by a flexible wall having a cross sectional shape resembling an "L" geometry as illustrated in FIG. 16. Moreover, support for the cushion in the sealing areal at the lower part of the mouth, may be formed by a flexible wall having a cross sectional shape resembling the "C" geometry as shown below in FIG. 17.

Similarly, with respect to at least the example clip shown in FIGS. 14, 18 and 19, two active portions of the clip's structure are the peripheral lip 3540 that form an effective cantilever over-hang portion and a middle transverse portion 3541 of the clip's periphery between the frame coupling surface 3539 and the cushion support surface 3538. Both of these components can act as springs and provide a sealing reaction force through their deformation. Distribution of the clip-contributed sealing force around the mouth may be governed by the clip's material and geometry. Moreover, the force may be controlled by the user depending on the amount of tightening of the headgear of the mask.

In this regard, the combination of a foam cushion and the flexible support structure of the clip can provide reasonable results. However, for achieving optimal seal comfort, the flexible clip may be provided with an oversized peripheral lip that increases the support of a foam cushion width that may be larger than the support surface of the peripheral lip. Such variations in the width of the peripheral lip can produce different reaction forces around the periphery of the mouth cushion. Beam and bending principles may show that, in isolation, a shorter peripheral lip will produce a stiffer mechanical system as there will be less clip deflection for a certain unit force than there will be for a longer peripheral lip.

Such a clip may be considered with reference to the cushion support structures of FIGS. 14, 18 and 19. Sizing of the width (shown in FIG. 18 as arrow LW) of the peripheral lip also allows for introducing variations in the seal geometry. For example, different (e.g., narrower) widths in the peripheral lip area proximate to the nose and mouth may help to achieve different reaction sealing forces in these areas. As illustrated in FIG. 18, the profile for the clip's peripheral lip may be changed to that shown by the dashed line. The resulting clip is illustrated in FIG. 19. As illustrated, a shorter lip width (shown at arrow SLW) may be provided at the peak of the nasal plateau region for less flexibility. A relatively longer lip width (shown as arrows LL) may be provided proximate the centrally open lip superior region COLS for more flexibility. As shown in FIG. 19, the reaction force of such a clip can vary around the periphery as a result of such changing widths of the peripheral lip or cantilever arm. In some such cases, the width of the cushion may be similarly varied. However, the width of the cushion may be relatively constant despite the change in support structure width around its periphery such as shown in FIG. 23. In this sense, the foam's geometry profile may not follow the clip's geometry exactly. As a result, the final force profile of the mask can be affected by the combination of the clip and the compressing foam.

Adjustments to flexibility around the sealing periphery may also be achieved by varying the thickness of the lip. For example, a lip thickness value along the sides of the mouth toward the nasal peak portion may be approximately double that of the thickness along the bottom of the mouth. Such a ratio can provide less flexibility in the nasal region and relatively more flexibility in the lip inferior region. In one such example, and depending on the clip materials, peripheral lip thickness may be in a range of about 1.5 mm to 2.5 mm, such as about a 2.2 mm (+/−0.1 mm) relatively constant thickness from the region proximate to the sides of the mouth to the nasal peak region. The region of the peripheral lip proximate to the lip inferior (around the bottom of the mouth) may be in the range of about 0.75 mm to 1.25 mm, such as about a relatively constant 1.0 mm (+/−0.1 mm) thickness.

Generally, the body depth (illustrated in FIG. 14 as arrow BD) may be relatively constant about the periphery of the clip. In the example of FIGS. 14, 18 and 19, the body depth of the clip (that portion that does not connect to the cushion or the frame) may be in a range, for example, from about 8 mm to 15 mm or for example a depth in a range of about 11 mm to 13 mm.

In some cases, additional features may be formed with or applied to the cushion support structure to further affect the performance of the seal. Such an example is illustrated with respect to the clip of FIG. 13, which is also shown applied to a frame in FIGS. 20 and 21. In the example of FIG. 13, the clip also contains extra cantilever protrusions 3561 that may further serve as cantilever springs. With these elements, the clip can press the foam into hard-to-seal areas such as the corners of the nose, effectively providing a variable level of cushion compliance.

As previously mentioned, the cushion support (clip or frame), or portions thereof, may be molded from different grades of thermoplastic elastomers TPE. Grades of different hardness may be used. Generally, a TPE material may be more beneficial to silicone as it may be more easily molded onto some cushions (e.g., foam) and its processing time may be faster than silicone. However, other elastic or flexible materials may be used such as thermoplastic polyurethane (TPU), thermoplastic polyurethane TPV or rubber, etc. By way of further example, in some cases, the flexible support structure (e.g., clip) may be formed with silicone, such as a room temperature vulcanizing RTV silicone.

As mentioned previously, because of their flexible nature, the cushion and cushion support structure (e.g., clip) work in unison to respond to the compression force imparted to the frame by the headgear vectors. However, the cushion, such as when foam is used, may play a greater part in conforming to the face of the user purely because it is the softer component and therefore may compress more. Eventually, when the headgear tension has been applied and the frame is pulled towards the patient's face, the foam and flexible support structure will reach an equilibrium shape, in which a seal is created.

Example cushions for the mask assemblies of the present technology are illustrated in FIGS. 24 and 25. The cushions may be foam and form a triangular or oval shaped ring. The corners may be rounded. In the example of FIG. 24, the cushion has a generally flat patient contact surface PCS. In some such cases, the edges may be rounded. For example, as illustrated in FIG. 25, the cushion profile along is periphery may have a generally curved patient contact surface PCS. Other cushion profiles may also be implemented. The frame or clip contact side of the cushion may be generally flat or otherwise conform to the contact surface of the cushion support structure.

With these example generally uni-planar cushions, when connected to the clip or frame as illustrated in FIGS. 26 and 27, the cushion may deform to a multi-planar shape as previously discussed that is better for sealing. The triangular shape, when so deformed, enables the cushion to produce its seal around the outer periphery of a portion of the nares, into the corners of the nose and around the side and the bottom of the mouth while maintaining a substantially under-the-nose configuration and providing for a centrally open lip superior region. Thus, the mask may have a substantially non-contact area in the central lip superior region between the upper vermillion and the columella in the sub-nasal region. Moreover, this non-contact region may be within the plenum chamber during use.

While the cushions of FIGS. 26 and 27 are generally uni-planar and are deformed by the frame or clip to have their multi-planar use configuration (e.g., with an nasolabial angle between the nasal plateau region and the mouth periphery region), in some cases the cushion or foam may be pre-formed or pre-cut in the multi-planar shape consistent with the shape of the clip or frame.

Generally, there should be an air tight seal between cushion and its support structure (e.g., the clip). Various methods may be employed to implement such a joining of the cushion. For example, the cushion may be adhered to the support structure such as with glue, spray adhesives or hotmelts, etc. In some cases, it may be adhered by ultrasonic welding. In some cases, the cushion may be sewn and adhered. The join may also be implemented with an intermediary material such as a tape (e.g., a double sided adhesive tape). In some cases, the support structure (e.g., clip) may be over molded to the cushion.

Similarly, such methods may be employed for joining the cushion to the frame, such as without an interfacing clip. In this regard, the frame may provide the shape forming structure and surface to hold the cushion (e.g., foam) in the desired profile for patient sealing. In such an embodiment, the cushion foam may provide some or all of the necessary spring and softness to effect the seal and provide comfort to the patient. Otherwise, some of the previously described flexible features (e.g., cantilever components of the clip) may be formed with the frame to assist with the seal and comfort effectiveness. In some such clip-free cases, some of the flexible properties of the clip may be imparted to the foam by using a secondary layer of cushion rather than the clip. Such a secondary cushion layer may be applied to the patient contact foam layer and may have different flexibility/rigidity properties when compared to the first foam layer. In such a case, the second layer of the dual cushion may be applied directly to the frame without the clip.

If the foam cushion is intended to be a throw away/replacable item (such as in the case of the cushion/clip combination), the cushion could be directly attached to the frame through an adhesive membrane located on the foam. In such a case, the cushion may be simply removed, and a different cushion, with a new adhesive strip, may then be attached to the reusable frame (or reusable clip). In some cases, the foam cushion and frame may be co-molded. In some such cases, the cushion and frame unit may then be discarded together.

In some examples, the cushion 3110 may include additional features. For example, as shown in FIG. 28, the cushion may include an indent, such as a scalloped notch 3763, such as in the nasal plateau region of the cushion. The indent may be formed by a semi-peripheral cut of an edge of the cushion in the nasal portion of the seal. In some examples, the cut may form a rising edge from a centrally lower position to a radially higher position. Such a semi-peripheral area may provide a cupping support around the nose. The cupping geometry may provide a greater surface area (bearing surface). In this regard, the scalloped shape feature may replicate the topography under the user's nose. As such, the scalloped notch may also improve sealing in the sub-nasal ridge area and may provide improved nasal comfort. It may also serve to minimize nose inflation. The feature may also provide a perceptively distinct landing area for patients to place their nose, resulting in a more intuitive set-up. In some cases, the notched area or the nasal plateau region may be marked to provide an indication of nasal location for user installation. For example, the area may have a distinct color with respect to the remaining areas of the cushion.

The shape of such a notch may be defined from any of the following anthropometric features: width between the labial insertions of the alar base; length of the ala; nasal ala-slope angle; inclination of the columella; nasal tip protrusion; width of nose. In some cases, the depth of the indent detail may be based on any of: the inclination of the columella; patient perception with respect to providing sufficient indication as to where the under nose section of the mask should be worn; sufficient surface to seal around the edge curvature of the nose; sufficient support around the periphery of the nose to prevent the nose from blowing out such as due to pressure from a pressure treatment.

Other versions of the geometry of the indent may include a simple chamfered edge following the periphery of the nose. When the foam has sufficient compliance for the chamfer to fit the nose an improved seal can result. Similarly, other variations in the overall triangular shape of the scalloped nasal feature may be achieved since foam has sufficient compliance to conform to facial features in a range of sizes.

As previously mentioned, the indent, such as the scalloped nasal detail, can effectively cup the lower periphery of the nose and may provide additional surface area for sealing and comfort. Thus, it may work in conjunction with other components of the mask assembly (clip and frame) during use to effectively serve as a seal. In terms of sealing and depending on the specific anthropology of the nose, the sealing interface may shift or extend or both, from under the nose to under and/or partially up the sides of the nose. In terms of comfort, the force applied to the nose from the headgear and the treatment pressure from the seal interface, may thereby be distributed over a larger surface area, resulting in better comfort.

The geometry of the indent in the foam cushion can change to accommodate a range of nasal sizes. A nose that is pressed into the scalloped detail, for example, during set-up of the mask will displace foam until the foam conforms to the nose. The flexible spring nature of the cushion support structure (e.g., clip and/or frame) can provide a resistive force at this stage to prevent the nose from fully pushing through the foam. Under treatment pressure, the foam can be pressed back against the nose which helps to provide an effective seal.

In some cases, the indent may be manufactured as part of a complete compression cutting process for the cushion. Alternatively, the feature may be manufactured by a secondary process such as thermoforming, ultrasonic welding or cutting. In some cases, the whole cushion including the scalloped nasal detail may be manufactured from a single compression cutting or thermoforming process.

In some further examples, the cushion may also include one or more protrusions. Such protrusion(s) may be included on the surface of the cushion. For example, one or more protrusions can be so disposed so that, when the mask is fit on the patient's face, the protrusions extend further out of the cushion into a portion of the patient's face. As such, the protrusions may provide additional structural support and a better seal. For example, a set (e.g., pair) of protrusions 3764, such as one or more appproximately oval projections or of another shape, are illustrated in the cushion and mask of FIGS. 29, 30 and 31. These protrusions are disposed so as to extend on the left and right sides of the nose. As such, they may assist with buttressing the cushion's seal at the difficult sealing areas on both sides of the nose. The protrusions, while useful, are optional. An effective seal in these difficult regions may also be achieved by other means, including increasing the thickness and varying the shape of the foam cushion in these areas. For example, a narrowing may be introduced at the sides of the nasal area of the cushion to facilitate a better seal.

As previously mentioned, the connection between the clip and frame may be implemented with various structures. Some examples are illustrated in FIGS. 32 through 35. Generally, in the case of an implementation of a clip, there should be an air tight seal between the clip and the frame. The cushion/clip assembly can be detachable from the frame so as to permit regular replacement of the cushion in the case that the cushion may have a shorter useful life when compared to the frame.

Some example connection structures for anchoring the clip to the frame may include: tongue and groove geometry; a stretchable periphery skirt to extend around an edge of the frame; a peripheral edge that connects by interference fit, such as one similar to air-tight food containers; a tongue and slot interface with secondary lip seal or gasket present. In some cases, the connection structures of the clip may correspond to existing mask frames to permit retrofitting of the cushion designs described herein with existing mask frames.

In the connector example of FIGS. 32A and 32B, the clip and frame may be coupled together by a bulbous ridge 3572 and channel 3574. For example, the frame may be formed with the channel and the clip may include the ridge. A cross sectional view of the ridge and channel may appear as a ball and socket. The soft flexible (e.g., TPE, silicone or other flexible material) bulbous ridge may be pressed into the rigid channel frame (e.g., plastic) to provide a seal and mechanical retention. Optionally snap fingers 3576 may also aid assembly and component de-molding.

In the connector example of FIGS. 33A and 33B, the clip and frame may be coupled together by a skirt 3578 and flange 3515 such as the flange extending continuously around the plenum chamber of the frame 3500. In such a case, the skirt 3578 of the clip may be a semi-rigid element (e.g., TPE, polypropylene or other similar semi-rigid material) continuously extending around the ring of the clip. Plying the skirt so as to cup it over the flange may then serve as a seal and provide mechanical retention.

In the connector example of FIG. 34, the clip and frame may be coupled together by a snap shoulder 3580 and engagement cavity 3582 continuously or semi-continuously extending around the periphery of the clip and frame. Such a snap may be formed on a rim of the clip 3535. The rim and snap may be displaced by a more rigid frame upon engagement, such as when the snap shoulder, which may be a semi-rigid material (e.g., plypropylene) is plied into the engagement cavity 3582. The surface engagement of the rim and frame may provide a seal and the snap shoulder and engagement cavity coupling can provide a mechanical retention.

In the connector example of FIGS. 35A and 35B, the clip and frame may be coupled together by a taper lock (shown in exploded view 3583). In such an example, a peripheral rim 3702 of the frame, which may be rigid, may be retained in a peripheral channel 3585 of the clip. A taper element 3586 of the frame may couple with a taper receiving channel 3587 of the clip, which may be flexible (e.g., silicone, TPE, etc). The taper element and the taper receiving channel may be formed so as to continuously or semi-continuously extend around the periphery of the clip and frame. The taper element and taper receiving channel may then aid mechanical retention of the frame and clip components.

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A mask apparatus for a respiratory treatment comprising:
   a frame adapted to couple with a respiratory treatment apparatus so as to permit communication of a pressurized gas to a respiratory system of a patient from the respiratory treatment apparatus; and a cushion adapted to couple with the frame, the cushion configured as a substantially under nose seal portion and a mouth seal portion, the under nose seal portion comprising a sub-nasal ridge formed as a semi-peripheral sealing boundary about both nares of the patient.

2. The mask apparatus of claim 1 wherein the cushion comprises a triangular ring having a common nasal and mouth aperture.

3. The mask apparatus of claim 2 wherein the cushion is foam.

4. The mask apparatus of claim 3 wherein the cushion and the frame form a common plenum chamber for sealing about the nares and mouth.

5. The mask apparatus of claim 1 wherein the cushion comprises a protrusion configured to ply adjacent to a nasal ala of the patient.

6. The mask apparatus of claim 1 wherein the cushion comprises left and right nasal ala protrusions.

7. The mask apparatus of claim 1 further comprising a cushion support clip, the cushion support clip configured to couple with the cushion and couple with the frame.

8. The mask apparatus of claim 7 wherein the cushion support clip comprises first and second opposing sides, and wherein the clip is configured to couple with the cushion on the first opposing side and to couple with the frame on the second opposing side.

9. The mask apparatus of claim 7 wherein the cushion support clip comprises a nasal plateau region and a mouth periphery region.

10. The mask apparatus of claim 9 wherein the nasal plateau region is approximately perpendicular to the mouth periphery region.

11. The mask apparatus of claim 9 wherein the cushion support clip comprises a bend region between the nasal plateau region and the mouth periphery region, the bend region forming an approximately nasolabial angle between the nasal plateau region and the mouth periphery region.

12. The mask apparatus of claim 11 wherein the bend region comprises a set of inwardly directing nasal protrusions.

13. The mask apparatus of claim 12 wherein the nasal protrusions are flexible.

14. The mask apparatus of claim 7 wherein the cushion support clip comprises first and second cushion support portions, the first and second cushion support portions being configured to provide different flexibility characteristics.

15. The mask apparatus of claim 14 wherein the first cushion support portion comprises a nasal support region and the second cushion support portion comprises a lateral mouth support region, the first cushion support portion having a higher rigidity characteristic with respect to the second cushion support portion.

16. The mask apparatus of claim 1 wherein the sub-nasal ridge includes a scalloped edge.

17. The mask apparatus of claim 1 wherein the cushion comprises a generally flat sealing surface.

18. The mask apparatus of claim 1 wherein the cushion comprises a generally curved sealing surface.

19. The mask apparatus of claim 1 further comprising a respiratory treatment apparatus configured to generate a controlled supply of breathable gas at a pressure above atmospheric pressure, the respiratory treatment apparatus including a gas delivery conduit coupled with the frame to direct the breathable gas to the frame.

20. A respiratory mask for delivering a respiratory gas treatment, the mask including a frame and cushion, the cushion adapted to couple with the frame, the cushion configured as a substantially under nose seal portion and a mouth seal portion, the cushion further defining a centrally open lip superior region.

21. The respiratory mask of claim 20 wherein the cushion comprises a nasal plateau region and a mouth periphery region, the cushion configured with an approximately nasolabial angle between the nasal plateau region and the mouth periphery region.

22. The respiratory mask of claim 21 wherein the cushion comprises a triangular ring having a common nasal and mouth aperture.

23. The respiratory mask of claim 20 wherein the cushion is foam.

24. The respiratory mask of claim 20 wherein the cushion and the frame form a common plenum chamber for sealing about the nares and mouth, the centrally open lip superior region being within the plenum chamber.

25. The respiratory mask of claim 20 wherein the cushion comprises a protrusion configured to ply adjacent to a nasal ala of the patient.

26. The respiratory mask of claim 20 wherein the cushion comprises left and right nasal ala protrusions.

27. The respiratory mask of claim 20 further comprising a clip to removably couple the cushion to the frame.

28. A respiratory mask for delivering a respiratory gas treatment, the mask including a frame and cushion, the cushion adapted to couple with the frame, the cushion configured as a substantially under nose seal portion and a mouth seal portion, the cushion further defining a centrally open lip superior region, further comprising a clip to removably couple the cushion to the frame, wherein the clip comprises flexible nasal protrusions.

29. The respiratory mask of claim 27 wherein the clip comprises first and second cushion support portions, the first and second cushion support portions being configured to provide different flexibility characteristics.

30. A mask apparatus for a respiratory treatment comprising:

a frame adapted to couple with a respiratory treatment apparatus so as to permit communication of a pressurized gas to a respiratory system of a patient from the respiratory treatment apparatus;

a cushion adapted to couple with the frame, the cushion configured as a substantially under nose seal portion and a mouth seal portion, the under nose seal portion comprising a sub-nasal ridge formed as a semi-peripheral sealing boundary about both nares of the patient; and a cushion support clip, the cushion support clip configured to couple with the cushion and couple with the frame, wherein the cushion support clip comprises first and second opposing sides, and wherein the clip is configured to couple with the cushion on the first opposing side and to couple with the frame on the second opposing side, and wherein the cushion support clip comprises a nasal plateau region and a mouth periphery region.

* * * * *